(12) United States Patent
Bannou et al.

(10) Patent No.: US 8,163,950 B2
(45) Date of Patent: *Apr. 24, 2012

(54) PROCESSES FOR THE PRODUCTION OF TRI-ORGANO-MONOALKOXYSILANES AND PROCESS FOR THE PRODUCTION OF TRI-ORGANO-MONOCHLOROSILANES

(75) Inventors: Tadashi Bannou, Tamano (JP); Shin Masaoka, Atsugi (JP); Yoshiki Hayakawa, Tokyo (JP)

(73) Assignees: Shin-Etsu Chemical Co., Ltd., Tokyo (JP); Hokko Chemical Industry Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/186,031

(22) Filed: Jul. 19, 2011

(65) Prior Publication Data

US 2011/0275849 A1 Nov. 10, 2011

Related U.S. Application Data

(62) Division of application No. 12/324,286, filed on Nov. 26, 2008, now Pat. No. 8,008,521, which is a division of application No. 10/495,075, filed as application No. PCT/JP02/11694 on Nov. 8, 2002, now Pat. No. 7,459,577.

(30) Foreign Application Priority Data

| Nov. 8, 2001 | (JP) | 2001-342924 |
| Dec. 20, 2001 | (JP) | 2001-387749 |
| Dec. 26, 2001 | (JP) | 2001-393755 |

(51) Int. Cl.
*C07F 7/04* (2006.01)
(52) U.S. Cl. .......... 556/435; 556/465; 556/480
(58) Field of Classification Search .......... 556/435, 556/465, 480
See application file for complete search history.

(56) References Cited

U.S. PATENT DOCUMENTS

| 4,593,112 A * | 6/1986 | Takamizawa et al. ........ 556/480 |
| 4,780,556 A * | 10/1988 | Hata et al. .................... 556/467 |
| 5,296,624 A * | 3/1994 | Larson et al. ................. 556/435 |

FOREIGN PATENT DOCUMENTS

| DE | 3013920 | * 10/1981 |
| JP | 2854832 | * 11/1996 |
| JP | 08311083 | * 11/1996 |

* cited by examiner

*Primary Examiner* — Sikarl Witherspoon
(74) *Attorney, Agent, or Firm* — B. Aaron Schulman, Esq.; Stites & Harbison PLLC

(57) ABSTRACT

A silane containing a bulky hydrocarbon group or groups R therein and having the formula (III)

$$R_{3-(x+y)}(R^1)_x(R^2)_y Si(OR^3)$$

can be produced by reacting a silane of the formula (I)

$$(R^1)_x(R^2)_y SiCl_{3-(x+y)}(OR^3)$$

with a Grignard reagent of the formula (II)

RMgX

Further, a tri-organo-chlorosilane of the formula (XIIa)

$$(R^1)(R^2)(R^3)SiCl$$

can be produced by reacting a tri-organo-silane of the formula (XIa)

$$(R^1)(R^2)(R^3)SiZ^1$$

with hydrochloric acid.
Furthermore, a tri-organo-monoalkoxysilane of the formula (XXIII)

$$R_{3-(x+y)}(R^1)_x(R^2)_y Si(OR^3)$$

can be produced when a silane of the formula (XXI)

$$(R^1)_x(R^2)_y SiCl_{4-(x+y)}$$

is reacted with a Grignard reagent of the formula (XXII)

RMgX with addition of and reaction with an alcohol or an epoxy compound during the reaction.

6 Claims, No Drawings

PROCESSES FOR THE PRODUCTION OF TRI-ORGANO-MONOALKOXYSILANES AND PROCESS FOR THE PRODUCTION OF TRI-ORGANO-MONOCHLOROSILANES

CROSS-REFERENCE TO RELATED APPLICATIONS

The present application is a divisional of U.S. application Ser. No.: 12/324,286, filed Nov. 26, 2008, now U.S. Pat. No. 8,008,521 which is a divisional of U.S. application Ser. No.: 10/495,075, filed Nov. 12, 2004, now U.S. Pat. No. 7,459,577 which is a 371 application based on PCT/JP02/11694, filed Nov. 8, 2002, all of said applications incorporated herein by reference.

TECHNICAL FIELD

This invention relates to a novel process capable of producing, easily and effectively, a tri-organo-mono(substituted or unsubstituted alkoxy)silane containing therein at least two bulky hydrocarbon groups likely to easily bring about a steric hindrance, such as a secondary or tertiary hydrocarbon group, including secondary or tertiary alkyl groups. The aforesaid silane may be useful for the production of a water-repellent and also for the production of a hydroxyl-protecting agent of silyl type for the protection of functional hydroxyl groups present in chemical intermediates formed in the organic syntheses.

This invention further relates to a novel process capable of producing, advantageously and easily on an industrial scale, a tri-organo-monochlorosilane, particularly a tri-organo-monochlorosilane containing therein a bulky hydrocarbon group or groups, such as a secondary or tertiary hydrocarbon group. The tri-organo-monochlorosilanes may be utilized as materials for the synthesis of silicone rubber and also as a silylating agent for protecting functional hydroxyl groups in the chemical intermediates formed in the organic syntheses done in the synthesis of medicines, agricultural chemicals and others.

BACKGROUND ART

As the methods for introducing organic groups (that is, organo-groups) such as an alkyl group, an aralkyl group or an aryl group or the like into silicon compounds, there is now generally employed such process wherein a Grignard reagent containing said organic group is reacted with an organo-substituted or organo-unsubstituted chlorosilane containing one to four chloro groups, thereby to produce an organo-silane containing one to four organo groups and also zero to three chloro groups. However, a bulky, secondary or tertiary hydrocarbon group likely to easily bring about a steric hindrance is not readily introducible into the said organo-substituted or organo-unsubstituted chlorosilane containing one to four chloro groups, by means of the process comprising reacting the Grignard reagent containing such bulky hydrocarbon group with said organo-substituted or organo-unsubstituted chlorosilane.

There is also known another process wherein a secondary or tertiary alkyl lithium is used, instead of such Grignard reagent, and is reacted with said organo-substituted or organo-unsubstituted chlorosilane (refer to J. Org. Chem. Vol. 43, p. 3649 (1978)).

For a process for the introduction of a secondary hydrocarbon group or a tertiary hydrocarbon group likely to easily cause the steric hindrance, onto a silicon atom of an organo-halosilane by means of the Grignard reaction, there is also known a process wherein a Grignard reagent containing a secondary or tertiary hydrocarbon group is reacted with the organo-halosilane in the presence of a catalyst comprising a copper compound or a cyanide compound or thiocyanic acid compound (refer to Japanese Patent Publication Hei-7-86115, Japanese Patent No. 2838342 and Japanese Patent No. 2854832).

Further, there is known a process for the synthesis of a dimethyl-monoalkoxy-arylsilane and a dimethyl-monoalkoxy-cyclohexylsilane, comprising reacting a dimethyl-monoalkoxy-chlorosilane with a Grignard reagent containing phenyl group, 1-naphthyl group or cyclohexyl group (refer to Zh. Obshch. Khim., 1987, 57(1), pp. 146-151 and Chemical Abstracts, Vol. 108, Par. 6072v). However, the Russian literature above-mentioned has no description of the production of a tri-organo-monoalkoxysilane containing at least two of the bulky hydrocarbon groups.

There is known an organo-hydrosilane compound having a silicon-hydrogen linkage, and there is also known a process comprising reacting such organo-hydrosilane compound with a Grignard reagent containing a tertiary hydrocarbon group (refer to Japanese Patent No. 3091992).

Further, there are many known processes for the production of tri-organo-monochlorosilanes containing a bulky hydrocarbon group. Main known processes proposed for such purpose are as follows.
(1) Process comprising reacting an organo-halosilane with a Grignard reagent in the presence of a catalyst to cause a Grignard reaction to produce a tri-organo-monochlorosilane intended, filtering the resulting reaction solution to remove therefrom the magnesium chloride deposited, and recovering the intended silane product (Japanese Patent Publication Hei-7-86115).
(2) Process according to the process (1) above, wherein the reaction solution resulting from the Grignard reaction is subjected directly to a distillation after the Grignard reaction was conducted with using a solvent made of polyalkyleneglycol dialkylether (Japanese Patent No. 2854832).
(3) Commercially available process adapted for industrial scale production, wherein the silicon-hydrogen linkage of a tri-organo-hydrosilane is chlorinated with chlorine.
(4) Process wherein the alkoxy group of a tri-organo-alkoxysilane is chlorinated with a chlorinating agent such as an acyl chloride, thionyl chloride, phosphorus trichloride, and the like.
(5) Process wherein the chlorination of a tri-organo-hydrosilane is effected by an exchange reaction between a tri-organo-hydrosilane and a chlorosilane in the presence of a catalyst (Japanese Patent No. 3131868).
(6) Process wherein a tri-organo-hydrosilane is reacted with hydrogen chloride gas in the presence of a transition metal of Group VIII or a complex thereof under anhydrous condition (Japanese Patent Prepublication Kokai Hei-6-157554).
(7) Process as described in J. Am. Chem. Soc., Vol. 68, p. 2282 (1946), wherein triethylsilanol is treated with a conc. hydrochloric acid under ice-cooling, thereby to afford triethylchlorosilane in 77% yield.
(8) Process as described in a book "Chemistry and Technology of Silicones", Page 86, (published in 1968 by ACADEMIC PRESS), wherein a trialkylalkoxysilane is treated with hydrogen chloride gas under anhydrous condition and converted into the corresponding chlorosilane.

However, in the above process (1) according to Japanese Patent Publication Hei-7-86115, the operation for the removal by filtration of the magnesium chloride by-produced is troublesome, with needs of additional treatment of magnesium chloride. In the process (2) above according to Japanese Patent No. 2854832, the use of the special solvent is necessary, so that this process is disadvantageous commercially in view of expensive cost. In the commercial process shown in (3) above, a chlorinated solvent is required as the reaction solvent, so that there is a serious problem for the environmental protections. In the chlorination process shown in (4) above, the generation of sulfur dioxide gas and other by-products is involved and is problematic in view of the environmental protections. In the process (5) above according to Japanese Patent No. 3131868, the inevitable formation of unnecessary by-products and the use of the catalyst are disadvantageous in economical point of view.

In the above process (6) according to Japanese Patent Pre-publication Kokai Hei-6-157554, the use of expensive metal catalyst is required and thus not advantageous in industrial operations. In the process (7) above according to the report of J. Am. Chem. Soc., Vol. 68, p. 2282 (1946), the silanol compound is to be treated with conc. hydrochloric acid under ice-cooling conditions, because the silanol is easily hydrolyzable and is difficult to be handled, so that the industrial practice of this process is not advantageous in economical point of view. The process (8) above according to "Chemistry and Technology of Silicones", p. 86, where the chlorination is to be effected with hydrogen chloride gas under anhydrous conditions, is still needed to be improved upon its industrial practice in respect of the safety and the operating efficiency, due to the necessary handling of hydrogen chloride gas. In consequence, all the known processes proposed in the prior art have some unavoidable defects.

Accordingly, there is a keen demand for creating any novel industrial process for the production of organo-chlorosilanes, which is able to work more easily and simply in a commercial scale.

For the purpose of producing the organosilanes containing a secondary or tertiary alkyl group or groups, the above-mentioned prior art process as shown in J. Org. Chem., Vol. 43, p. 3649 shall require that the organo-substituted or organo-unsubstituted chlorosilane is reacted with a secondary or tertiary alkyl lithium. This prior art process cannot be suitable if it is applied on an industrial scale operation with handling of a large amount of materials, because the handlings of metallic lithium and of alkyl lithium as prepared therefrom are very dangerous.

In cases of the prior art processes as taught by Japanese Patent Publication Hei-7-86115, Japanese Patent No. 2838342 or Japanese Patent No. 2854832, these processes shall require that a Grignard reaction is carried out by using the catalyst made of a copper compound, a cyanide compound or a thiocyanate compound. In these processes, the use of highly toxic compounds as the catalyst is required, thus bringing about problems on safety. In the another prior art process shown in Japanese Patent No. 3091992, an organo-hydrosilane compound having a silicon-hydrogen linkage is used as the starting material, and this starting material is often expensive. Further, in the other process of the prior art where a trichlorosilane is to be used as the starting material, the starting material is a low boiling, inflammable substance, so that special caution is required for handling it, thus causing problems on safety and economy.

Therefore, it is now keenly required to provide any novel process for producing a tri-organo-monoalkoxysilane compound having at least two bulky hydrocarbon groups each likely to cause the steric hindrance, such as a secondary or tertiary alkyl group, which process can be operated in a facile way on industrial scale, safely and in a high yield.

DISCLOSURE OF THE INVENTION

We, the inventors of this invention, have eagerly proceeded our investigations with the intention of producing a tri-organo-monoalkoxysilane having at least two bulky hydrocarbon groups therein. As a result, we have now confirmed that, in case when tetrachlorosilane (namely, silicon tetrachloride) is subjected to a Grignard reaction with isopropyl magnesium chloride as Grignard reagent, for example, in a usual manner and under usual reaction conditions, the desired Grignard reaction expectedly can hardly progress to an extent that the desired tri(isopropyl)-monochlorosilane can be produced.

Apart from the fact we have confirmed in the above, however, we have now found, for the first time, that the desired tri-(isopropyl)-monomethoxy, monoethoxy or mono-n-butoxysilane can be produced in a high yield, if tetrachlorosilane is reacted at first with methanol, ethanol or n-butanol to replace one of the four chloro groups of tetrachlorosilane by methoxy, ethoxy or n-butoxy group, to produce monomethoxy, monoethoxy or mono-n-butoxytrichlorosilane, and if the resulting monoalkoxytrichlorosilane so produced is then contacted and reacted with isopropyl magnesium chloride in a usual manner and under usual reaction conditions for the Grignard reaction, to result in that the desired Grignard reaction can progress efficiently to attain the intended result. We have now further found that the above-mentioned reaction procedure, has no need to use any catalyst and no need to provide the presence of a copper compound, cyanide compound or thiocyanate compound for effecting the progress and achievement of the intended Grignard reaction.

We now have furthermore found that the desired Grignard reaction can also proceed efficiently when tetrachlorosilane is at first reacted with, for example, ethylene oxide or benzyl alcohol and when the resulting mono(2-chloroethoxy)-trichlorosilane or monobenzyloxytrichlorosilane so produced is then subjected to the Grignard reaction, for example, with using isopropyl magnesium chloride or sec-butyl magnesium chloride as the Grignard reagent, in a usual manner and under usual reaction conditions for the Grignard reaction, and that the desired tri-(isopropyl or sec-butyl)-mono(2-chloroethoxy or benzyloxy)silane can thus be produced in a high yield. In addition, we have found that the tri-(isopropyl)-monomethoxy, monoethoxy or mono-n-butoxysilane, as well as the tri-(isopropyl or sec-butyl)-mono(2-chloroethoxy or benzyloxy)silane as produced in the above Grignard reaction can then be converted into tri-(isopropyl or sec-butyl)-monochlorosilane, if it is treated by a known chlorinating method, for example, with a chlorinating agent such as thionyl chloride.

The latter compound, tri-(isopropyl or sec-butyl)-monochlorosilane, is known as a hydroxyl-protecting agent of silyl type to protect a functional hydroxyl group of chemical intermediate compounds usable in organic syntheses and also is known as a useful starting material for the production of various water-repellents of silicone type.

We have proceeded our further investigations. As a result, we have now found generically that an organo-unsubstituted or a mono-organo or di-organo-mono(alkoxy, cycloalkyloxy or aralkyloxy)-tri, di or monochlorosilane having the general formula (I)

$$(R^1)_x(R^2)_y SiCl_{3-(x+y)}(OR^3) \quad (I)$$

wherein $R^1$ stands for a primary, secondary or tertiary alkyl group, a cycloalkyl group, an alkenyl group, an alkynyl group, an aryl group or an aralkyl group, $R^2$ stands for a secondary alkyl group, a tertiary alkyl group, a cycloalkyl group or an aryl group, and $R^3$ stands for a primary or secondary alkyl group, a cycloalkyl group or an aralkyl group, or the group —OR³ stands for a 2-substituted or unsubstituted-2-chloroethoxy group of the formula (A)

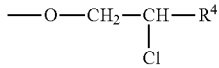
(A)

where R⁴ is a hydrogen atom or an alkyl group of 1-8 carbon atoms or R⁴ is an alkoxymethylene group or an alkenyloxymethylene group or an aryloxymethylene group of the formula —CH₂—O—R⁵ where R⁵ is a straight or branched chain alkyl group of 1-20 carbon atoms or an alkenyl group of 2-10 carbon atoms or an aryl group, particularly phenyl group or naphthyl group, and x stands for an integer of 0 or 1, and y stands for an integer of 0, 1 or 2, provided that the integers for x and y are to be within the range of 0≦(x+y)≦2, is able to easily react with a Grignard reagent of the general formula (II)

RMgX    (II)

wherein R stands for a secondary alkyl group, a tertiary alkyl group or a cycloalkyl group, or R stands for an alkyl-substituted aromatic hydrocarbon group of which the alkyl substituent is bonding to a carbon atom present in the aromatic hydrocarbon group with said carbon atom being adjacent to the carbon atom of the aromatic hydrocarbon group that is bonding to the magnesium atom, and X stands for a chlorine, bromine or iodine atom, in a usual manner and under usual reaction conditions for the Grignard reaction, and without the necessity of adding any catalyst in the reaction system; and that there can thus be produced a tri-organo-mono(alkoxy, cycloalkyloxy or aralkyloxy)silane containing the bulky hydrocarbon group or groups R therein and having the general formula (III)

(III)

wherein R¹, R², R³ have the same meanings as defined above, R is the secondary alkyl group, tertiary alkyl group or cycloalkyl group as defined above or the alkyl-substituted aromatic hydrocarbon group as defined above, and x and y stand for the above-defined integers.

It is presumed that the chloro group, which is bonding to the silicon atom of the silane via the silicon-chlorine linkage present in the organo-unsubstituted or mono-organo- or di-organo-mono(alkoxy, cycloalkyloxy or aralkyloxy)-tri, di or monochlorosilane of the general formula (I), has got an increased reactivity to the bulky hydrocarbon group due to certain function of the alkoxy group, cycloalkyloxy group or aralkyloxy group OR³ existing in said silane of the formula (I).

According to a first aspect of this invention, therefore, there is provided a process for the production of a tri-organo-mono(alkoxy, cycloalkyloxy or aralkyloxy)silane containing a bulky hydrocarbon group or groups R therein and having the general formula (III)

(III)

wherein R¹ stands for a primary, secondary or tertiary alkyl group, a cycloalkyl group, an alkenyl group, an alkynyl group, an aryl group or an aralkyl group, R² stands for a secondary alkyl group, a tertiary alkyl group, a cycloalkyl group or an aryl group, and R³ stands for a primary or secondary alkyl group, a cycloalkyl group or an aralkyl group, or the group —OR³ stands for a 2-substituted or unsubstituted-2-chloroethoxy group of the formula (A)

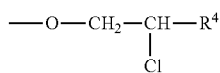
(A)

where R⁴ is a hydrogen atom or an alkyl group of 1-8 carbon atoms, or R⁴ is an alkoxymethylene group, an alkenyloxymethylene group or an aryloxymethylene group of the formula —CH₂—O—R⁵ where R⁵ is a straight or branched chain alkyl group of 1-20 carbon atoms or an alkenyl group of 2-10 carbon atoms or an aryl group, and wherein R stands for a secondary alkyl group, a tertiary alkyl group or a cycloalkyl group, or R is an alkyl-substituted aromatic hydrocarbon group as defined below, and x stands for an integer of 0 or 1 and y stands for an integer of 0, 1 or 2, provided that these integers for x and y are to be within the range of 0≦(x+y)≦2, characterized in that the process comprises reacting an organo-unsubstituted or mono-organo or di-organo-mono(alkoxy, cycloalkyloxy or aralkyloxy)-tri, di or monochlorosilane of the general formula (I)

(I)

wherein R¹, R², R³, x and y have the same meanings as defined above, with a Grignard reagent of the general formula (II)

RMgX    (II)

wherein R stands for a secondary alkyl group, a tertiary alkyl group or a cycloalkyl group as defined above, or R stands for an alkyl-substituted aromatic hydrocarbon group of which the alkyl substituent is bonding to a carbon atom present in the aromatic hydrocarbon group, with said carbon atom being adjacent to the carbon atom of the aromatic hydrocarbon group that is bonding to the magnesium atom, and X stands for a chlorine, bromine or iodine atom.

The above process of the first aspect of this invention will now be explained in detail.

First of all, the explanation is given on the following three methods (i)-(iii) for preparing the organo-unsubstituted or mono-organo or di-organo-mono(alkoxy, cycloalkyloxy or aralkyloxy)-tri, di or monochlorosilane of the general formula (I) which is to be used as the starting compound in the process of the first aspect of this invention.

Method (i): The organo-unsubstituted or mono-organo or di-organo-mono(alkoxy, cycloalkyloxy or aralkyloxy)-tri, di or monochlorosilane of the general formula (I) to be used as the starting compound, where group —OR³ in the formula (I) does not mean the 2-substituted or unsubstituted-2-chloroethoxy group of the formula (A), may be prepared by reacting tetrachlorosilane or a di or mono-organo-di or trichlorosilane of the general formula (IV)

(IV)

wherein R¹ and R² have the same meanings as defined above and x and y are integers as defined above, with an alcohol of the general formula (V)

R³OH    (V)

wherein R³ stands for the primary or secondary alkyl group, cycloalkyl group or aralkyl group as defined above.

The tetrachlorosilane is the compound of the formula (B)

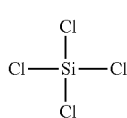
(B)

which is included in the compounds of formula (IV) above (namely, the case of x=y=0).

The substituent $R^1$ in the compound of the general formula (IV) above is a primary, secondary or tertiary alkyl group, a cycloalkyl group, an alkenyl group, an alkynyl group, an aryl group or an aralkyl group.

The primary, secondary or tertiary alkyl group for $R^1$ is preferably a straight or branched chain alkyl group of 1-20 carbon atoms, typically those straight or branched chain alkyl groups such as methyl group, ethyl group, n-propyl group, isopropyl group, n-butyl group, isobutyl group, sec-butyl group, tert-butyl group, n-pentyl group, isopentyl group, sec-pentyl group, 1,1-dimethylpropyl group, n-hexyl group, n-heptyl group, n-octyl group, 2-ethylhexyl group, n-dodecyl group and n-octadecyl group.

The cycloalkyl group for $R^1$ may typically be the one of 3-8 carbon atoms such as cyclopentyl group and cyclohexyl group. Typical alkenyl group for $R^1$ may be vinyl group, methallyl group, allyl group, etc. Typical alkynyl group as $R^1$ may be ethynyl group, 1-propynyl group, etc.

The aryl group for $R^1$ may typically be phenyl group, alkyl-substituted phenyl group, such as o-tolyl group, m-tolyl group, p-tolyl group, 2,3-xylyl group, 2,4-xylyl group, 2,5-xylyl group, 2,6-xylyl group, 3,4-xylyl group, 3,5-xylyl group, mesityl group, 1-naphthyl group, etc. The aralkyl group for $R^1$ may typically be a lower alkyl group substituted with phenyl group, such as benzyl group, phenylethyl group (namely phenethyl group), etc.

The substituent $R^2$ is a secondary alkyl group, a tertiary alkyl group, a cycloalkyl group or an aryl group. The secondary alkyl group for $R^2$ may the one of 3-10 carbon atoms and typically isopropyl group, sec-butyl group, sec-pentyl group, etc.

The tertiary alkyl group $R^2$ may be those of 4-10 carbon atoms and typically tert-butyl group, 1,1-dimethylpropyl group, 1-ethyl-1-methylpropyl group, 1,1,2-trimethylpropyl group and 1,1-diethylpropyl group.

The cycloalkyl group for $R^2$ may be those of 3-8 carbon atoms such as cyclopentyl group and cyclohexyl group. The aryl group for $R^2$ may be those of the same range as exemplified for the group $R^1$ above.

Preferred examples of the compound of the formula (IV) may include tetrachlorosilane, methyltrichlorosilane, ethyltrichlorosilane, vinyltrichlorosilane, phenyltrichlorosilane, diphenyldichlorosilane, phenylmethyldichlorosilane, etc.

The alcohol $R^3OH$ of the formula (V) to be reacted with the compound of the formula (IV) is a primary or secondary alkylalcohol or a cycloalkylalcohol or an aralkyl alcohol.

Of the alcohol of the formula (V) above, the alkylalcohol (alkanol) may typically be methanol, ethanol, n-propanol, isopropanol, n-butanol, isobutanol, sec-butanol, etc. The cycloalkylalcohol may typically be cyclopentylalcohol and cyclohexylalcohol. Typical aralkylalcohol may be benzylalcohol, phenylethylalcohol, etc.

The step for the alkoxylation or aralkyloxylation reaction, where the tetrachlorosilane or organo-chlorosilane of the general formula (IV) is reacted with the alcohol of the formula (V), is preferably effected by using 0.5-2 moles, particularly 0.5-1.5 moles of the alcohol of the formula (V) for the reaction with 1 mole of the tetrachlorosilane or organochlorosilane of the formula (IV). The step for the alkoxylation or aralkyloxylation reaction may be conducted either in the absence of a solvent or in an aprotic organic solvent. As such aprotic organic solvent, there may be used an ether-type solvent such as diethylether, tetrahydrofuran and the like which is conventionally used in Grignard reactions, or a hydrocarbon-type solvent such as hexane, toluene and the like. These solvents may be used alone or in any combination of two or more of them. The reaction step for the alkoxylation or aralkyloxylation may be carried out at a temperature in the range of $-10°$ C.-$150°$ C., preferably $0°$ C.-$100°$ C. The reaction with the alcohol of the formula (V) will generates hydrogen chloride gas as a by-product, and it is necessary to expel the gas from the reaction system.

After the completion of the alkoxylation or aralkyloxylation reaction above, there is obtained a reaction solution containing a mono(alkoxy, cycloalkyloxy or aralkyloxy)-chlorosilane of the general formula (I) thus produced. The compound of the general formula (I) can be recovered by subjecting the reaction solution to a fractional distillation under atmospheric or a reduced pressure. Otherwise, said reaction solution may be used as such for the first aspect process of this invention which corresponds to the subsequent Grignard reaction step.

Method (ii): Among the organo-unsubstituted or mono or di-organo-mono(alkoxy, cycloalkyloxy or aralkyloxy)-tri, di or monochlorosilanes of the general formula (I) to be used as the starting compound, the organo-unsubstituted or mono or di-organo-monoalkoxy-tri, di or monochlorosilane of the general formula (I')

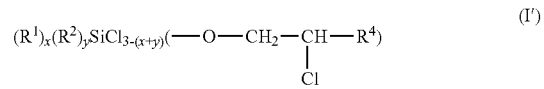
(I')

wherein $R^1$, $R^2$ and $R^4$ have the same meanings as defined above and x and y are the integers as defined above can be prepared by a method comprising reacting tetrachlorosilane or a di or mono-organo-di or trichlorosilane of the general formula (IV)

(IV)

wherein $R^1$ and $R^2$ have the same meanings as defined above and x and y are the integers as defined above, with an alkylene oxide or a glycidylether of the general formula (VI)

(VI)

wherein $R^4$ is a hydrogen atom or an alkyl group of 1-8 carbon atoms or $R^4$ stands for an alkoxymethylene group, an alkenyloxymethylene group or aryloxymethylene group of the formula $-CH_2-O-R^5$ where $R^5$ is a straight or branched chain alkyl group of 1-20 carbon atoms or an alkenyl group of 2-10 carbon atoms or an aryl group.

The compound of the general formula (VI), where $R^4$ is a hydrogen atom or an alkyl group, is an alkylene oxide of the general formula (VI) which is an epoxy compound having the epoxy group at the end of the hydrocarbon chain, such as ethylene oxide, propylene oxide, etc.

On the other hand, the compound of the general formula (VI), where $R^4$ is an alkoxymethylene group or an alkenyloxymethylene group or an aryloxymethylene group of the formula (A), is the compound of the general formula (VI) which is a glycidylether. It may, for example, be butylglycidyl ether, glycidylmethylether, etc.

Other examples of the glycidylether of the general formula (VI) may include 2-ethylhexylglycidylether, octadecylglycidylether; allylglycidylether; glycidylphenylether.

The intended reaction in the Method (ii) may proceed by reacting 0.5-2 moles of an alkylene oxide or a glycidylether of the general formula (VI) with 1 mole of tetrachlorosilane or the organo-chlorosilane of the general formula (IV) in the absence of a solvent or in an aprotic organic solvent, for example in diethylether, at a temperature of –10° C.-150° C. A mixed solvent of hydrocarbons may also be used. The epoxy group of the compound of the general formula (VI), when it is reacted with the organo-chlorosilane of the general formula (IV), can undergo the ring-opening, thereby to incorporate therein the chloro group of the chlorosilane compound of the general formula (IV), and thus there is generated no hydrogen chloride gas, in contrast to Method (i) above.

Method (iii): The organo-unsubstituted or mono or di-organo-mono (alkoxy, cycloalkyloxy or aralkyloxy)-tri, di or monochlorosilane of the general formula (I) where the group —$OR^3$ of the formula (I) does not mean the 2-substituted or unsubstituted-2-chloroethoxy group, which is to be used as the starting compound, may also be prepared by a method comprising mixing an alkoxysilane of the general formula (VII)

$$(R^1)_x(R^2)_y Si(OR^3)_z Cl_{4-(x+y+z)} \quad (VII)$$

wherein $R^1$, $R^2$ and $R^3$ have the same meanings as defined above, x stands for an integer of 0 or 1, and y stands for an integer of 0, 1 or 2, provided that the integers for x and y are within the range of $0 \leq (x+y) \leq 2$; and z stands for an integer of 2, 3 or 4, provided that it is within the range of $2 \leq (x+y+z) \leq 4$, with tetrachlorosilane or a di or mono-organo-di or trichlorosilane of the general formula (IV)

$$(R^1)_x(R^2)_y SiCl_{4-(x+y)} \quad (IV)$$

wherein $R^1$ and $R^2$ have the same meanings as defined above and x and y are the integers as defined above, and effecting a disproportionation reaction between the tetrachlorosilane or silane of the general formula (IV) and the alkoxysilane of the general formula (VII).

$R^1$ and $R^2$ of the alkoxysilane of the general formula (VII) stand for the same substituents as $R^1$ and $R^2$ of the general formulae (I) or (IV). Concrete examples of the alkoxysilane of the general formula (VII) may be tetramethoxysilane, tetraethoxysilane, methyltrimethoxysilane, methyltriethoxysilane, vinyltrimethoxysilane, vinyltriethoxysilane, phenyltrimethoxysilane, phenyltriethoxysilane, diphenyldimethoxysilane, diphenyldiethoxysilane, phenylmethyldimethoxysilane, and phenylmethyldiethoxysilane, etc.

In the disproportionation reaction above, tetrachlorosilane or a chlorosilane of the general formula (IV) and the alkoxysilane of the general formula (VII) are preferably reacted in their proportions such that 0.1-3 moles, particularly 0.2-1.5 moles of an alkoxysilane of the general formula (VII) are used for 1 mole of tetrachlorosilane or a chlorosilane of the general formula (IV) so as to induce a highest proportion of a monochlorosilane of the general formula (I) to be produced. The disproportionation reaction may be conducted in the absence of a solvent at 0-50° C., preferably 10-30° C.

The reaction solution resulting from the step of the disproportionation reaction is a reaction solution of a mixture containing as a main constituent therein the organo-unsubstituted or mono or di-organo-mono(alkoxy or cycloalkyloxy or aralkyloxy)chlorosilane of the general formula (I), that is, the intended product of this reaction step, and further containing the unreacted starting materials and by-products in which two or more chloro groups have been alkoxylated.

For the process of the first aspect of this invention which corresponds to the Grignard reaction step subsequent to said disproportionation step, it is possible that the reaction solution as obtained from said disproportionation reaction may be used as such. However, the said reaction solution may be once subjected to a fractional distillation to isolate a purified product of the mono(alkoxy or cyclo-alkyloxy or aralkyloxy)silane of the general formula (I), which is then used in the process of the first aspect invention.

As is clear from the above explanation, the process of the first aspect of this invention is carried out by reacting a chlorosilane compound of the general formula (I) with a Grignard reagent of the general formula (II).

In the organometallic compound which is the Grignard reagent of the general formula (II), the bulky hydrocarbon group R contained therein is either a secondary alkyl group, a tertiary alkyl group or a cycloalkyl group, or the hydrocarbon group R may be an aromatic hydrocarbon group having an alkyl substituent as defined hereinbefore. Examples of said secondary alkyl group include isopropyl group, sec-butyl group and sec-pentyl group. Examples of said tertiary alkyl group include tert-butyl group, 1,1-dimethylpropyl group, 1-methyl-1-ethylpropyl group, 1,1-diethylpropyl group and 1,1,2-trimethylpropyl group. As the said cycloalkyl group, there are listed cyclopentyl group, cyclohexyl group, 1-methylcyclopentyl group, 1-methylcyclohexyl group and 1-ethylcyclohexyl group.

For the aromatic hydrocarbon group having alkyl substituent, there are exemplified an alkyl-substituted phenyl group such as o-tolyl group, 2,3-xylyl group, 2,4-xylyl group, 2,5-xylyl group, 2,6-xylyl group and mesityl group, and 1-naphtyl group and the like. X stands for a halogen atom which is chlorine, bromine or iodine.

As concrete examples of the Grignard reagent of the general formula (II), there may be given isopropyl magnesium chloride, isopropyl magnesium bromide, isopropyl magnesium iodide; sec-butyl magnesium chloride, sec-butyl magnesium bromide, sec-butyl magnesium iodide; sec-pentyl magnesium chloride, sec-pentyl magnesium bromide, sec-pentyl magnesium iodide; cyclopentyl magnesium chloride, cyclopentyl magnesium bromide, cyclopentyl magnesium iodide; cyclohexyl magnesium chloride, cyclohexyl magnesium bromide, cyclohexyl magnesium iodide; tert-butyl magnesium chloride, tert-butyl magnesium bromide, tert-butyl magnesium iodide; 1,1-dimethylpropyl magnesium chloride, 1,1-dimethylpropyl magnesium bromide, 1,1-dimethylpropyl magnesium iodide; 1-methyl-1-ethylpropyl magnesium chloride, 1-methyl-1-ethylpropyl magnesium bromide, 1-methyl-1-ethylpropyl magnesium iodide; 1,1-diethylpropyl magnesium chloride, 1,1-diethylpropyl magnesium bromide, 1,1-diethylpropyl magnesium iodide; 1,1,2-trimethylpropyl magnesium chloride, 1,1,2-trimethylpropyl magnesium bromide, 1,1,2-trimethylpropyl magnesium iodide; 1-methylcyclopentyl magnesium chloride, 1-methylcyclopentyl magnesium bromide, 1-methylcyclopentyl magnesium iodide; 1-methylcyclohexyl magnesium chloride, 1-methylcyclohexyl magnesium bromide, 1-methylcyclohexyl magnesium iodide; 1-ethylcyclohexyl magnesium chloride, 1-ethylcyclohexyl magnesium bromide, 1-ethylcyclohexyl magnesium iodide; o-tolyl magnesium chloride, o-tolyl magnesium bromide, o-tolyl magnesium iodide; 2,3-xylyl magnesium chloride, 2,3-xylyl magnesium bromide, 2,3-xylyl magnesium iodide; 2,4-xylyl magnesium chloride, 2,4-xylyl magnesium bromide, 2,4-xylyl magnesium iodide; 2,5-xylyl magnesium chloride, 2,5-xylyl magnesium bromide, 2,5-xylyl magnesium iodide; 2,6-xylyl magnesium chloride, 2,6-xylyl magnesium bromide, 2,6-xylyl magnesium iodide; mesityl magnesium chloride, mesityl magnesium bromide, mesityl magnesium iodide; 1-naphthyl magnesium chloride, 1-naphthyl magnesium bromide or 1-naphthyl magnesium iodide, but these examples never limit the usable Grignard reagent thereto.

The Grignard reaction in the process according to the first aspect of this invention may be carried out in an ether-type solvent or in a mixed solvent of an ether-type solvent with an aprotic organic solvent as above-mentioned. As such aprotic organic solvent, there may be exemplified hydrocarbon-type solvent such as hexane, heptane, toluene, xylene, etc. The Grignard reagent of the general formula (II) may preferably be used for the Grignard reaction in a proportion of 1-10 moles, preferably 1-5 moles per 1 mole of the mono(alkoxy or cycloalkyloxy or aralkyloxy)chlorosilane of the general formula (I).

In case when the reaction solution resulting from the reaction step for the preparation of the starting compound of the general formula (I) is to be used as such for the Grignard reaction, and when a reaction solvent is used, it is usually desirable that the Grignard reaction is effected in the same ether-type solvent or same mixed solvent of the ether-type solvent with aprotic organic solvent as the reaction solvent which was used in the preceding step. The Grignard reaction may preferably be conducted at a temperature in the range of −10° C.-150° C., preferably of 20° C.-150° C. It is furthermore desirable that the Grignard reaction is carried out under an inert gas atmosphere such as nitrogen, argon, or the like, because the presence of oxygen in the reaction system brings about a reaction with the Grignard reagent, thus resulting in lowering of the yield of the desired reaction product.

The Grignard reaction may be conducted in a usual manner for 1-29 hours until completion of the reaction. Subsequently, an appropriate amount of a saturated aqueous ammonium chloride solution or a dilute sulfuric acid is added and mixed in the resulting reaction solution. Thus, the inorganic magnesium salt as deposited in the reaction solution can be dissolved in said aqueous ammonium chloride solution or dilute sulfuric acid. The organic layer is then separated from the aqueous layer, and the organic layer so separated is subjected to a fractional distillation (namely, rectification) under atmospheric or reduced pressure, whereby there can be recovered a fraction consisting of the desired tri-organo-mono(alkoxy, cycloalkyloxy or aralkyloxy)silane of the general formula (III).

In case when an organo-unsubstituted or mono(alkoxy, cycloalkyloxy or aralkyloxy)-trichlorosilane is used as the starting compound of the general formula (I) and is reacted a Grignard reagent having a highly bulky tertiary alkyl group such as tert-butyl group, there is a possibility that the yield of the desired tri-organo-substituted-mono(alkoxy, cycloalkyloxy or aralkyloxy)silane so produced might be only very low, even if the Grignard reaction is conducted for a long period of time.

The tri-organo-mono(alkoxy, cycloalkyloxy or aralkyloxy)silane of the general formula (III) can also be represented by the general formula (III')

wherein $R^1$, $R^2$, $R^3$, R, x and y each have the same meanings as defined above.

As concrete examples of the mono(alkoxy, cycloalkyloxy or aralkyloxy)silane derivatives of the general formula (III) as produced by the process of the first aspect of this invention, there are enumerated triisopropylmethoxysilane, triisopropylethoxysilane, triisopropylisopropoxysilane, triisopropyl-n-butoxysilane, triisopropyl-2-chloroethoxysilane, triisopropylbenzyloxysilane, tri-sec-butylmethoxysilane, tri-sec-butylethoxysilane, tri-sec-butylisopropoxysilane, tri-sec-butyl-n-butoxysilane, tri-sec-butyl-2-chloroethoxysilane, tri-sec-butylbenzyloxysilane, tricyclohexylmethoxysilane, tricyclohexylethoxysilane, tricyclohexylisopropoxysilane, tricyclohexyl-n-butoxysilane, tricyclohexyl-2-chloroethoxysilane, tricyclohexylbenzyloxysilane, tri-o-tolylmethoxysilane, tri-o-tolylethoxysilane, tri-o-tolylisopropoxysilane, tri-o-tolyl-n-butoxysilane, tri-o-tolyl-2-chloroethoxysilane, tri-o-tolylbenzyloxysilane, diisopropylmethylmethoxysilane, diisopropylmethylethoxysilane, diisopropylmethylisopropoxysilane, diisopropylmethyl-n-butoxysilane, diisopropylmethyl-2-chloroethoxysilane, diisopropylmethylbenzyloxysilane, diisopropylvinylmethoxysilane, diisopropylvinylethoxysilane, diisopropylvinylisopropoxysilane, diisopropylvinyl-n-butoxysilane, diisopropylvinyl-2-chloroethoxysilane, diisopropylvinylbenzyloxysilane, diisopropylphenylmethoxysilane, diisopropylphenylethoxysilane, diisopropylphenylisopropoxysilane, diisopropylphenyl-n-butoxysilane, diisopropylphenyl-2-chloroethoxysilane, diisopropylphenylbenzyloxysilane, di-sec-butylmethylmethoxysilane, di-sec-butylmethylethoxysilane, di-sec-butylmethylisopropoxysilane, di-sec-butylmethyl-n-butoxysilane, di-sec-butylmethyl-2-chloroethoxysilane, di-sec-butylmethylbenzyloxysilane, di-sec-butylvinylmethoxysilane, di-sec-butylvinylethoxysilane, di-sec-butylvinylisopropoxysilane, di-sec-butylvinyl-n-butoxysilane, di-sec-butylvinyl-2-chloroethoxysilane, di-sec-butylvinylbenzyloxysilane, di-sec-butylphenylmethoxysilane, di-sec-butylphenylethoxysilane, di-sec-butylphenylisopropoxysilane, di-sec-butylphenyl-n-butoxysilane, di-sec-butylphenyl-2-chloroethoxysilane, di-sec-butylphenylbenzyloxysilane, dicyclohexylmethylmethoxysilane, dicyclohexylmethylethoxysilane, dicyclohexylmethylisopropoxysilane, dicyclohexylmethyl-n-butoxysilane, dicyclohexylmethyl-2-chloroethoxysilane, dicyclohexylmethylbenzyloxysilane, dicyclohexylvinylmethoxysilane, dicyclohexylvinylethoxysilane, dicyclohexylvinylisopropoxysilane, dicyclohexylvinyl-n-butoxysilane, dicyclohexylvinyl-2-chloroethoxysilane, dicyclohexylvinylbenzyloxysilane, dicyclohexylphenylmethoxysilane, dicyclohexylphenylethoxysilane, dicyclohexylphenylisopropoxysilane, dicyclohexylphenyl-n-butoxysilane, dicyclohexylphenyl-2-chloroethoxysilane, dicyclohexylphenylbenzyloxysilane, di-o-tolylmethylmethoxysilane, di-o-tolylmethylethoxysilane, di-o-tolylmethylisopropoxysilane, di-o-tolylmethyl-n-butoxysilane, di-o-tolylmethyl-2-chloroethoxysilane, di-o- tolylmethylbenzyloxysilane, di-o-tolylvinylmethoxysilane, di-o-tolylvinylethoxysilane, di-o-tolylvinylisopropoxysilane, di-o-tolylvinyl-n-butoxysilane, di-o-tolylvinyl-2-chloroethoxysilane, di-o-tolylvinylbenzyloxysilane, di-o-tolylphenylmethoxysilane, di-o-tolylphenylethoxysilane, di-o-tolylphenylisopropoxysilane, di-o-tolylphenyl-n-butoxysilane, di-o-tolylphenyl-2-chloroethoxysilane, di-o-tolylphenylbenzyloxysilane, isopropyldiphenylmethoxysilane, isopropyldiphenylethoxysilane, isopropyldiphenylisopropoxysilane, isopropyldiphenyl-n-butoxysilane, isopropyldiphenyl-2-chloroethoxysilane, isopropyldiphenylbenzyloxysilane, sec-butyldiphenylmethoxysilane, sec-butyldiphenylethoxysilane, sec-butyldiphenylisopropoxysilane, sec-butyldiphenyl-n-butoxysilane, sec-butyldiphenyl-2-chloroethoxysilane, sec-butyldiphenylbenzyloxysilane, cyclohexyldiphenylmethoxysilane, cyclohexyldiphenylethoxysilane, cyclohexyldiphenylisopropoxysilane, cyclohexyldiphenyl-n-butoxysilane, cyclohexyldiphenyl-2-chloroethoxysilane, cyclohexyldiphenylbenzyloxysilane, o-tolyldiphenylmethoxysilane, o-tolyldiphenylethoxysilane, o-tolyldiphenylisopropoxysilane, o-tolyldiphenyl-n-butoxysilane, o-tolyldiphenyl-2-chloroethoxysilane, o-tolyldiphenylbenzyloxysilane, tert-butyldiphenylmethoxysilane, tert-butyldiphenylethoxysilane, tert-butyldiphenylisopropoxysilane, tert-butyldiphenyl-n-butoxysilane, tert-butyldiphenyl-2-chloroethoxysilane, tert-butyl-diphenylbenzyloxysilane, tert-butylphenylmethylmethoxysilane, tertbutylphenylmethylethoxysilane, tert-butylphenylmethylisopropoxysilane, tert-butylphenylmethyl-n-butoxysilane, tert-butylphenylmethyl-2-chloroethoxysilane, and the like, but they limit by no means limit the scope of the silane derivatives of the formula (III) thereto.

Among the silane derivatives of the formula (III) which can be produced by the process of the first aspect of this invention, tri-isopropyl-monoalkoxysilane, tri-sec-butylmonoalkoxysilane and tri-cyclohexyl-monoalkoxysilane are particularly useful as materials for the synthesis of tri-organo-chlorosilanes which are a silylating agent to be used for protecting functional hydroxyl groups of chemical intermediate compounds as produced in the various processes for the synthetic production of medicines, and others; and also they are useful for the other useful applications.

As is clear from the above explanations, the step of preparing a mono(methoxy, ethoxy, isopropoxy, n-butoxy or benzyloxy or 2-chloroethoxy)-trichlorosilane of the formula (I) with starting from a relatively inexpensive tetrachlorosilane SiCl₄ can be carried out by reacting the tetrachlorosilane with 1 molar proportion of, for example, methanol, ethanol, n-butanol, isopropanol or benzyl alcohol or ethylene oxide, etc., in the absence of a solvent or in an ether-type organic solvent conventionally used for Grignard reactions (the organic solvent may be a mixed solvent comprising an ether and an aprotic aromatic hydrocarbon solvent such as toluene).

The subsequent step of producing a desired tri-organo-mono(alkoxy, cycloalkyloxy or aralkyloxy)silane of the formula (III) having three of the secondary alkyl groups, cycloalkyl groups or the alkyl-substituted aromatic hydrocarbon groups as defined above can next be carried out in a way such that the mono-(organo-oxy)-trichlorosilane compound of the formula (I) as produced in the above step or the reaction solution containing said mono-(organo-oxy)-trichlorosilane compound of the formula (I) is reacted with a Grignard reagent of the formula (II) which is containing a secondary alkyl group or a cycloalkyl group or alkyl-substituted aromatic hydrocarbon group. Moreover, it is advantageous that said mono(alkoxy or cycloalkoxy or aralkyloxy)-trichlorosilane compound of the formula (I) so produced in the preceding step as an intermediate product can directly be used for the subsequent step even without making isolation of it from the reaction solution obtained in the preceding step, and that it is thus possible to conduct the above-mentioned preceding step and the subsequent step in a successive or consecutive manner.

According to a second aspect of this invention, therefore, there is provided a process for the production of a tri-organo-mono(alkoxy, cycloalkyloxy or aralkyloxy)silane of the general formula (IIIa)

(IIIa)

wherein $R^{3a}$ stands for a straight or branched chain alkyl group of 1-6 carbon atoms or a cycloalkyl group or an aralkyl group and $R^a$ stands for a secondary alkyl group or a cycloalkyl group or an alkyl-substituted aromatic hydrocarbon group as defined below, or for the production of a tri-organo-mono(2-substituted or unsubstituted-2-chloroethoxy)silane of the general formula (IIIb)

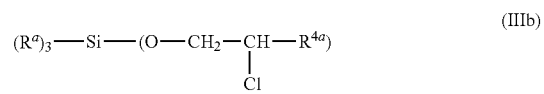

(IIIb)

wherein $R^{4a}$ stands for a hydrogen atom or an alkyl group of 1-8 carbon atoms, or $R^{4a}$ stands for a $(C_1\text{-}C_{20})$ alkyloxymethylene group, a $(C_2\text{-}C_{10})$ alkenyloxymethylene group or an aryloxymethylene group, and $R^a$ is as defined above and stands for a secondary alkyl group or a cycloalkyl group, or $R^a$ is an alkyl-substituted aromatic hydrocarbon group as defined below, characterized in that the process comprises a first step of reacting tetrachlorosilane with an alcohol of the formula (Va)

$$R^{3a}\text{—OH} \quad (Va)$$

wherein $R^{3a}$ has the same meaning as defined above, or with an alkylene oxide or a glycidylether of the formula (VIa)

(VIa)

wherein $R^{4a}$ has the same meaning as defined above, in the absence of any solvent or in the presence of an ether-type solvent or an aromatic hydrocarbon solvent usually usable for the Grignard reaction, thereby to produce either a mono (alkoxy or cycloalkyloxy or aralkyloxy)-trichlorosilane of the formula (Ia)

(Ia)

wherein $R^{3a}$ has the same meaning as defined above, or a mono(2-substituted or unsubstituted-2-chloroethoxy)-trichlorosilane of the formula (Ib)

(Ib)

wherein the group $R^{3b}O$— stands for the 2-substituted or unsubstituted-2-chloroethoxy group of the formula (A')

(A')

where $R^{4a}$ has the same meaning as defined above; and a second step of admixing the reaction solution resulting from said first step and containing therein either the mono(alkoxy or cycloalkyloxy or aralkyloxy)-trichlorosilane of the formula (Ia) as produced or the mono(2-substituted or unsubstituted-2-chloroethoxy)-trichlorosilane of the formula (Ib) as produced, with a Grignard reagent of the formula (II')

(II')

wherein $R^a$ stands for a secondary alkyl group or a cycloalkyl group, or $R^a$ stands for an alkyl-substituted aromatic hydrocarbon group of which the alkyl substituent is bonding to a carbon atom present in the aromatic hydrocarbon group, with said carbon atom being adjacent to the carbon atom of the aromatic hydrocarbon group that is bonding to the magnesium atom, and X stands for a chlorine, bromine or iodine atom, and subsequently effecting the intended Grignard reaction between the compound of the formula (Ia) or (Ib) and the Grignard reagent of the formula (II'), to produce the silane compound of the formula (IIIa) or (IIIb).

In the process of the second aspect of this invention, the first step thereof, which is effected for preparing the starting compound of formula (Ia) or (Ib) usable to be used for the first aspect process of this invention, may be carried out in the same manner as that of the aforesaid Method (i) or Method (ii), wherein tetrachlorosilane or an organo-chlorosilane compound of the general formula (IV) is reacted with an alcohol $R^3OH$ of the general formula (V) or an alkylene oxide or a glycidylether of the general formula (VI). The second step of this second aspect process of this invention may be carried out in the same manner as that explained for the first aspect process of this invention.

In accordance with the production processes of the first and second aspects of this invention, there can be produced easily and efficiently a tri-organo-mono(alkoxy or cycloalkyloxy or aralkyloxy)silane compound having at least two bulky hydrocarbon groups therein, without the necessity of using a lithium reagent which is difficult to be handled, and also without the necessity of using the highly toxic catalysts.

Apart from our investigations about the first and second aspects of this invention, we now have also eagerly proceeded our investigations with the intention of developing a novel process for the production of a tri-organo-monochlorosilane. In the related prior art, there was a common knowledge that when a tri-organo-silane compound having a hydrolyzable group is treated with hydrochloric acid added thereto, it is hydrolyzed to form a silanol which can then be dehydrated and condensed to be converted into siloxane compounds.

Unexpectedly, however, we have now found, as a result of our investigations now made, that a tri-organo-silane can be converted into a tri-organo-chlorosilane if hydrochloric acid is reacted with the tri-organo-silane under an appropriate condition. Our third aspect of this invention has now been accomplished on the basis of on this finding.

Thus, according to a third aspect of this invention, there is provided a process for the production of a tri-organo-monochlorosilane of the general formula (XIIa)

(XIIa)

wherein $R^1$, $R^2$ and $R^3$ are the same as or different from each other and each stand for a primary, secondary or tertiary alkyl group, a cycloalkyl group, an alkenyl group, an alkynyl group, an aralkyl group or an aryl group, but wherein $R^1$, $R^2$ and $R^3$ each and all do not represent methyl group at the same time, or for the production of a tri-organo-monochloro-silane of the general formula (XIIb)

(XIIb)

wherein $R^1$ and $R^2$ have the same meanings as defined above and $R^{3a}$ is a secondary alkyl group or a tertiary alkyl group or a cycloalkyl group, or $R^{3a}$ is an alkyl-substituted aromatic hydrocarbon group of which the alkyl substituent is bonding to a carbon atom present in the aromatic hydrocarbon group, with said carbon atom being adjacent to the carbon atom of the aromatic hydrocarbon group that is bondable to a magnesium atom, characterized in the process comprises reacting hydrochloric acid with a tri-organo-silane compound of the formula (XIa)

(XIa)

wherein $R^1$, $R^2$ and $R^3$ each have the same meanings as defined above and $Z^1$ is a hydrolyzable group, or particularly a tri-organo-silane compound containing the bulky hydrocarbon group $R^{3a}$ therein and having the formula (XIb)

(XIb)

wherein $R^1$, $R^2$ and $R^{3a}$ have the same meanings as defined above and $Z^2$ is a primary or secondary alkyloxy group, a cycloalkyloxy group or an aralkyloxy group, or $Z^2$ is a 2-substituted or unsubstituted-2-chloroethoxy group of the formula (A)

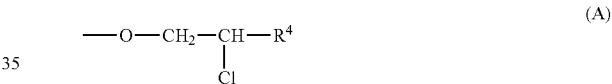

(A)

where $R^4$ is a hydrogen atom or an alkyl group of 1-8 carbon atoms, or $R^4$ is an alkoxymethylene group, an alkenyloxymethylene group or an aryloxymethylene group of the formula $—CH_2—O—R^5$ where $R^5$ is a straight or branched chain alkyl group of 1-20 carbon atoms or an alkenyl group of 2-10 carbon atoms or an aryl group, thereby to produce a tri-organo-monochlorosilane of the formula (XIIa) or a tri-organo-monochlorosilane of the formula (XIIb).

It is to be noted that the definitions of $R^1$ and $R^2$ for the general formula (XIa) or (XIb) according to the third aspect of this invention are broader than those of $R^1$ and $R^2$ as given for the general formula (I) according to the first aspect process of this invention.

The hydrolyzable group $Z^1$ in the tri-organo-silane compounds of the general formula (XIa) to be used in the process of the third aspect of this invention is an substituted or unsubstituted alkoxy group, a cycloalkyloxy group, an aralkyloxy group, an acyloxy group, amino group, an inorganic acid ester residue, or a pseudohalogen group, particularly cyano group. Examples of the alkoxy group as the hydrolyzable group $Z^1$ may include methoxy group, ethoxy group, n-propoxy group, isopropoxy group, n-butoxy group, sec-butoxy group, isobutyloxy group, n-hexyloxy group, cyclohexyloxy group, n-octyloxy group, 2-ethylhexyloxy group, 3-methylbutoxy group, phenoxy group, 2-chloroethoxy group, 2-chloro-3-n-butoxypropoxy group, etc., but they do not limit the scope of the group $Z^1$ thereto.

As typical example of an acyloxy group for the hydrolyzable group $Z^1$, there is given acetoxy group, and as amino group, there are not only simple amino group, but also dimethylamino, diethylamino, di-n-propylamino, diisopropylamino, di-n-butylamino and di-n-octylamino groups, etc. Example of the ester residue of an inorganic acid for $Z^1$ is sulfuric acid ester residue, etc. As examples of pseudohalogen group for $Z^1$, there are cyano group, thiocyano group, isothiocyano group, etc., but they do not limit the scope of such group. Moreover, the chlorination reaction of the process of the third aspect of this invention is particularly suitable for the preparation of a tri-organo-monochlorosilane having a bulky hydrocarbon substituent and having the general formula (XIb).

The organo groups $R^1$, $R^2$ and $R^3$ of the tri-organo-silane compound of the general formula (XIa) to be used as the starting compound in the third aspect process of this invention may be equal to each other or are different from each other, and they may be a primary, secondary or tertiary alkyl group, a cycloalkyl group, an alkenyl group, an alkynyl group, or an aralkyl group or an aryl group.

The alkyl group for $R^1$, $R^2$ or $R^3$ of the general formula (XIa) may preferably be a straight or branched chain alkyl group of 1-20 carbon atoms and concretely may be methyl group, ethyl group, n-propyl group, isopropyl group, n-butyl group, isobutyl group, sec-butyl group, tert-butyl group, n-pentyl group, isopentyl group, sec-pentyl group, 1,1-dimethylpropyl group, n-hexyl group, n-heptyl group, n-octyl group, 2-ethylhexyl group, n-dodecyl group, n-octadecyl group and others. In a case where the alkyl group as $R^1$, $R^2$, $R^3$ is a secondary or tertiary alkyl group, it may be a secondary or tertiary alkyl group as shown hereinafter for the group $R^{3a}$. The cycloalkyl group for $R^1$, $R^2$ or $R^3$ in the general formula (XIa) may be that of 3-8 carbon atoms such as cyclopentyl group, cyclohexyl group, and others. As the alkenyl group for $R^1$, $R^2$ or $R^3$ in the general formula (XIa), there may be listed vinyl group, methallyl group, allyl group and others. As the alkynyl group for $R^1$, $R^2$ or $R^3$, there may be listed ethynyl group, 1-propynyl group and others. As the aryl group for $R^1$, $R^2$ or $R^3$, there may be exemplified phenyl group, an alkyl-substituted phenyl group, such as o-tolyl group, m-tolyl group, p-tolyl group, 2,3-xylyl group, 2,4-xylyl group, 2,5-xylyl group, 2,6-xylyl group, 3,4-xylyl group, 3,5-xylyl group, mesityl group, or 1-naphthyl group, etc. As the aralkyl group for $R^1$, $R^2$ or $R^3$, there may be mentioned a phenyl-substituted lower alkyl group, for example, benzyl group, phenylethyl group (namely, phenethyl group), and the like.

The organo group $R^1$ and $R^2$ in the tri-organo-silane compound of the general formula (XIb) may be the same as those for $R^1$ and $R^2$ of the general formula (XIa). The organo group $R^{3a}$ of the compound of the general formula (XIb) is a secondary alkyl group, a tertiary alkyl group or a cycloalkyl group, or an alkyl-substituted aromatic hydrocarbon group. The secondary alkyl group as $R^{3a}$ is preferably that of 3-10 carbon atoms, such as, for example, isopropyl group, sec-butyl group and sec-pentyl group. The tertiary alkyl group as $R^{3a}$ is preferably that of 4-10 carbon atoms, such as, for example, tert-butyl group, 1,1-dimethylpropyl group, 1-methyl-1-ethylpropyl group, 1,1-diethylethyl group, 1,1,2-trimethylpropyl group and the like. The cycloalkyl group as $R^{3a}$ is preferably those of 3-8 carbon atoms, such as, for example, cyclopentyl group, cyclohexyl group, 1-methylcyclopentyl group, 1-methylcyclohexyl group, 1-ethylcyclohexyl group, etc. The alkyl-substituted aromatic hydrocarbon group for $R^{3a}$ is preferably that of 7-10 carbon atoms, such as an alkyl-substituted phenyl group, for example, o-tolyl group, 2,3-xylyl group, 2,4-xylyl group, 2,5-xylyl group, 2,6-xylyl group, mesityl group, or 1-naphthyl group, and others.

In the process of the third aspect of this invention, hydrochloric acid may be used in a proportion of 1-50 moles of hydrogen chloride per 1 mole of the starting tri-organo-silane compound of the general formula (XIa) or (XIb). The concentration of the hydrochloric acid depends upon the hydrolyzability of the tri-organo-chlorosilane produced of the general formula (XIIa) or (XIIb). The available range of the concentration of hydrochloric acid may be from 10% (by weight) to the saturated concentration (37% by weight), within which an appropriate concentration of HCl can be chosen. In a case where the resulting tri-organo-monochlorosilane product of the general formula (XIIa) or (XIIb) is highly hydrolyzable, it is desirable to use a large amount of hydrochloric acid having a high hydrogen chloride concentration. It is also possible to use hydrochloric acid in combination with hydrogen chloride gas. The reaction temperature for the chlorination reaction may be −20° C.-100° C., preferably −10° C.-50° C.

In the process of the third aspect of this invention, the reaction with hydrochloric acid may be carried out in an organic solvent. As the organic solvent, there may be mentioned an alcohol solvent, such as methanol, ethanol; or an aliphatic hydrocarbon solvent, such as hexane, heptane; or an aromatic hydrocarbon solvent, such as toluene, benzene, xylene; or an ether solvent, such as tetrahydrofuran, and the like. The organic solvent may be added to the reaction medium, either alone or in combination. In a case where an organic solvent is used, the concentration of the organic solvent in the reaction medium is not particularly limited. However, if a protic solvent such as alcohols is used, the concentration of the protic organic solvent is possible to be limited, depending on the hydrolyzability of the intended product.

As concrete examples of the tri-organo-silane compound of the general formula (XIa) or (XIb) to be used as the starting compound for the process of the third aspect of this invention, there may be listed, first of all, triethylmethoxysilane, including triisopropylmethoxysilane, triisopropylethoxysilane, triisopropylisopropoxysilane, triisopropyl-n-butoxysilane, triisopropyl-2-chloroethoxysilane, triisopropyl-3-methylbutoxysilane, triisopropylbenzyloxysilane, tri-sec-butylmethoxysilane, tri-sec-butylethoxysilane, tri-sec-butylisopropoxysilane, tri-sec-butyl-n-butoxysilane, tri-sec-butyl-2-chloroethoxysilane, tri-sec-butyl-3-methylpentyloxysilane, tri-sec-butylbenzyloxysilane, tricyclohexylmethoxysilane, tricyclohexylethoxysilane, tricyclohexylisopropoxysilane, tricyclohexyl-n-butoxysilane, tricyclohexyl-2-chloroethoxysilane, tricyclohexyl-2-cyclohexylethoxysilane, tricyclohexylbenzyloxysilane, tri-o-tolylmethoxysilane, tri-o-tolylethoxysilane, tri-o-tolylisopropoxysilane, tri-o-tolyl-n-butoxysilane, tri-o-tolyl-2-chloroethoxysilane, tri-o-tolyl-2-o-tolylethoxysilane, tri-o-tolylbenzyloxysilane, diisopropylmethylmethoxysilane, diisopropylmethylethoxysilane, diisopropylmethylisopropoxysilane, diisopropylmethyl-n-butoxysilane, diisopropylmethyl-2-chloroethoxysilane, diisopropylmethyl-3-methylbutoxysilane, diisopropylmethylbenzyloxysilane, diisopropylvinylmethoxysilane, diisopropylvinylethoxysilane, diisopropylvinylisopropoxysilane, diisopropylvinyl-n-butoxysilane, diisopropylvinyl-2-chloroethoxysilane, diisopropylvinyl-3-methylbutoxysilane, diisopropylvinylbenzyloxysilane, diisopropylphenylmethoxysilane, diisopropylphenylethoxysilane, diisopropylphenylisopropoxysilane, diisopropylphenyl-n-butoxysilane, diisopropylphenyl-2-chloroethoxysilane, diisopropylphenyl-3-methylbutoxysilane, diisopropylphenylbenzyloxysilane, di-sec-butylmethylmethoxysilane, di-sec-butylmethylethoxysilane, di-sec-butylmethylisopropoxysilane, di-sec-butylmethyl-n-butoxysilane, di-sec-butylmethyl-2-chloroethoxysilane, di-sec-butylmethyl-3- methylpentyloxysilane, di-sec-butylmethylbenzyloxysilane, di-sec-butylvinylmethoxysilane, di-sec-butylvinylethoxysilane, di-sec-butylvinylisopropoxysilane, di-sec-butylvinyl-n-butoxysilane, di-sec-butylvinyl-2-chloroethoxysilane, di-sec-butylvinyl-3-methylpentyloxysilane, di-sec-butylvinylbenzyloxysilane, di-sec-butylphenylmethoxysilane, di-sec-butylphenylethoxysilane, di-sec-butylphenyl isopropoxysilane, di-sec-butylphenyl-n-butoxysilane, di-sec-butylphenyl-2-chloroethoxysilane, di-sec-butylphenyl-3-methylpentyloxysilane, di-sec-butylphenylbenzyloxysilane, dicyclohexylmethylmethoxysilane, dicyclohexylmethylethoxysilane, dicyclohexylmethylisopropoxysilane, dicyclohexylmethyl-n-butoxysilane, dicyclohexylmethyl-2-chloroethoxysilane, dicyclohexylmethyl-2-cyclohexylethoxysilane, dicyclohexylmethylbenzyloxysilane, dicyclohexylvinylmethoxysilane, dicyclohexylvinylethoxysilane, dicyclohexylvinylisopropoxysilane, dicyclohexylvinyl-n-butoxysilane, dicyclohexylvinyl-2-chloroethoxysilane, dicyclohexylvinyl-2-cyclohexylethoxysilane, dicyclohexylvinylbenzyloxysilane, dicyclohexylphenylmethoxysilane, dicyclohexylphenylethoxysilane, dicyclohexylphenylisopropoxysilane, dicyclohexylphenyl-n-butoxysilane, dicyclohexylphenyl-2-chloroethoxysilane, dicyclohexylphenyl-2-cyclohexylethoxysilane, dicyclohexylphenylbenzyloxysilane, di-o-tolylmethylmethoxysilane, di-o-tolylmethylethoxysilane, di-o-tolylmethylisopropoxysilane, di-o-tolylmethyl-n-butoxysilane, di-o-tolylmethyl-2-chloroethoxysilane, di-o-tolylmethyl-2-o-tolylethoxysilane, di-o-tolylmethylbenzyloxysilane, di-o-tolylvinylmethoxysilane, di-o-tolylvinylethoxysilane, di-o-tolylvinylisopropoxysilane, di-o-tolylvinyl-n-butoxysilane, di-o-tolylvinyl-2-chloroethoxysilane, di-o-tolylvinyl-2-o-tolylethoxysilane, di-o-tolylvinylbenzyloxysilane, di-o-tolylphenylmethoxysilane, di-o-tolylphenylethoxysilane, di-o-tolylphenylisopropoxysilane, di-o-tolylphenyl-n-butoxysilane, di-o-tolylphenyl-2-chloroethoxysilane, di-o-tolylphenyl-2-o-tolylethoxysilane, di-o-tolylphenylbenzyloxysilane, isopropyldimethylmethoxysilane, isopropyldimethylethoxysilane, isopropyldimethylisopropoxysilane, isopropyldimethyl-n-butoxysilane, isopropyldimethyl-2-chloroethoxysilane, isopropyldimethyl-3-methyl butoxysilane, isopropyldimethylbenzyloxysilane, isopropyldivinylmethoxysilane, isoprpyldivinylethoxysilane, isopropyldivinylisopropoxysilane, isopropyldivinyl-n-butoxysilane, isopropyldivinyl-2-chloroethoxysilane, isopropyldivinyl-3-methylbutoxysilane, isopropyldivinylbenzyloxysilane, isopropyldiphenylmethoxysilane, isopropyldiphenylethoxysilane, isopropyldiphenylisopropoxysilane, isopropyldiphenyl-n-butoxysilane, isopropyldiphenyl-2-chloroethoxysilane, isopropyldiphenyl-3-methylbutoxysilane, isopropyldiphenylbenzyloxysilane, sec-butyldimethylmethoxysilane, sec-butyldimethylethoxysilane, sec-butyldimethylisopropoxysilane, sec-butyldimethyl-n-butoxysilane, sec-butyldimethyl-2-chloroethoxysilane, sec-butyldimethyl-3-methylpentyloxysilane, sec-butyldimethylbenzyloxysilane, sec-butyldivinylmethoxysilane, sec-butyldivinylethoxysilane, sec-butyldivinylisopropoxysilane, sec-butyldivinyl-n-butoxysilane, sec-butyldivinyl-2-chloroethoxysilane, sec-butyldivinyl-3-methylpentyloxysilane, sec-butyldivinylbenzyloxysilane, sec-butyldiphenylmethoxysilane, sec-butyldiphenylethoxysilane, sec-butyldiphenylisopropoxysilane, sec-butyldiphenyl-n-butoxysilane, sec-butyldiphenyl-2-chloroethoxysilane, sec-butyldiphenyl-3-methylpentyloxysilane, sec-butyldiphenylbenzyloxysilane, cyclohexyldimethylmethoxysilane, cyclohexyldimethylethoxysilane, cyclohexyldimethylisopropoxysilane, cyclohexyldimethyl-n-butoxysilane, cyclohexyldimethyl-2-chloroethoxysilane, cyclohexyldimethyl-2-cyclohexylethoxysilane, cyclohexyldimethylbenzyloxysilane, cyclohexyldivinylmethoxysilane, cyclohexyldivinylethoxysilane, cyclohexyldivinylisopropoxysilane, cyclohexyldivinyl-n-butoxysilane, cyclohexyldivinyl-2-chloroethoxysilane, cyclohexyldivinyl-2-cyclohexylethoxysilane, cyclohexyldivinylbenzyloxysilane, cyclohexyldiphenylmethoxysilane, cyclohexyldiphenylethoxysilane, cyclohexyldiphenylisopropoxysilane, cyclohexyldiphenyl-n-butoxysilane, cyclohexyldiphenyl-2-chloroethoxysilane, cyclohexyldiphenyl-2-cyclohexylethoxysilane, cyclohexyldiphenylbenzyloxysilane, o-tolyldimethylmethoxysilane, o-tolyldimethylethoxysilane, o-tolyldimethylisopropoxysilane, o-tolyldimethyl-n-butoxysilane, o-tolyldimethyl-2-chloroethoxysilane, o-tolyldimethyl-2-o-tolylethoxysilane, o-tolyldimethylbenzyloxysilane, o-tolyldivinylmethoxysilane, o-tolyldivinylethoxysilane, o-tolyldivinylisopropoxysilane, o-tolyldimethyl-n-butoxysilane, o-tolyldivinyl-2-chloroethoxysilane, o-tolyldivinyl-2-o-tolylethoxysilane, o-tolyldivinylbenzyloxysilane, o-tolyldiphenylmethoxysilane, o-tolyldiphenylethoxysilane, o-tolyldiphenylisopropoxysilane, o-tolyldiphenyl-n-butoxysilane, o-tolyldiphenyl-2-chloroethoxysilane, o-tolyldiphenyl-2-o-tolylethoxysilane, o-tolyldiphenylbenzyloxysilane, tert-butyldimethylmethoxysilane, tert-butyldimethylethoxysilane, tert-butyldimethylisopropoxysilane, tert-butyldimethyl-n-butoxysilane, tert-butyldimethyl-2-chloroethoxysilane, tert-butyldimethyl-3,3-dimethylbutoxysilane, tert-butyldimethylbenzyloxy silane, tert-butyldivinylmethoxysilane, tert-butyldivinylethoxysilane, tert-butyldivinylisopropoxysilane, tert-butyldivinyl-n-butoxysilane, tert-butyldivinyl-2-chloroethoxysilane, tert-butyldivinyl-3,3-dimethylbutoxysilane, tert-butyldivinylbenzyloxysilane, tert-butyldiphenylmethoxysilane, tert-butyldiphenylethoxysilane, tert-butyldiphenylisopropoxysilane, tert-butyldiphenyl-n-butoxysilane, tert-butyldiphenyl-2-chloroethoxysilane, tert-butyldiphenyl-3,3-dimethylbutoxysilane, tert-butyldiphenylbenzyloxysilane, tert-butylvinylmethylmethoxysilane, tert-butylvinylmethylethoxysilane, tert-butylvinylmethylisopropoxysilane, tert-butylvinylmethyl-n-butoxysilane, tert-butylvinylmethyl-2-chloroethoxysilane, tert-butylvinylmethyl-3,3-dimethyl-n-butoxysilane, tert-butylphenylmethylmethoxysilane, tert-butylphenylmethylethoxysilane, tert-butylphenylmethylisopropoxysilane, tert-butylphenylmethyl-n-butoxysilane, tert-butylphenylmethyl-2-chloroethoxysilane, tert-butylphenylmethyl-3,3-dimethylbutoxysilane, and others.

The unsubstituted or substituted alkoxy groups above-exemplified, such as methoxy group, ethoxy group, isopropoxy group, 2-chloroethoxy group, butoxy group, present in the silane compound of the general formula (XIa) or (XIb) can be replaced by a chloro group by the treatment with hydrochloric acid in the process of the third aspect of this invention to give the corresponding tri-organo-monochlorosilane.

As concrete examples of the tri-organo-monochlorosilanes produced by the third aspect process of this invention, there may be listed triethylchlorosilane, tri-n-propylchlorosilane, triisopropylchlorosilane, tri-n-butylchlorosilane, triisobutylchlorosilane, tri-sec-butylchlorosilane, tri-tert-butylchlorosilane, tri-n-octylchlorosilane, tricyclopentylchlorosilane, tricyclohexylchlorosilane, trimethallylchlorosilane, tri-o- tolylchlorosilane, tri-2,3-xylylchlorosilane, tri-2,4-xylylchlorosilane, tri-2,5-xylylchlorosilane, tri-2,6-xylylchlorosilane, tri-3,4-xylylchlorosilane, tri-3,5-xylylchlorosilane, trimesitylchlorosilane, methyldi-n-propylchlorosilane, methyldiisopropylchlorosilane, methyldi-n-butylchlorosilane, methyldiisobutylchlorosilane, methyldi-sec-butylchlorosilane, methyldi-tert-butylchlorosilane, methyldi-n-octylchlorosilane, methyldicyclopentylchlorosilane, methyldicyclohexylchlorosilane, methyldimethallylchlorosilane, methyldi-o-tolylchlorosilane, methyldi-2,3-xylylchlorosilane, methyldi-2,4-xylylchlorosilane, methyldi-2,5-xylylchlorosilane, methyldi-2,6-xylylchlorosilane, methyldi-3,4-xylylchlorosilane, methyldi-3,5-xylylchlorosilane, methyldimesitylchlorosilane, vinyldiethylchlorosilane, vinyldi-n-propylchlorosilane, vinyldiisopropylchlorosilane, vinyldi-n-butylchlorosilane, vinyldiisobutylchlorosilane, vinyldi-sec-butylchlorosilane, vinyldi-tert-butylchlorosilane, vinyldi-n-octylchlorosilane, vinyldicyclopentylchlorosilane, vinyldicyclohexylchlorosilane, vinyldimethallylchlorosilane, vinyldi-o-tolylchlorosilane, vinyldi-2,3-xylylchlorosilane, vinyldi-2,4-xylylchlorosilane, vinyldi-2,5-xylylchlorosilane, vinyldi-2,6-xylylchlorosilane, vinyldi-3,4-xylylchlorosilane, vinyldi-3,5-xylylchlorosilane, vinyldimesitylchlorosilane, phenyldiethylchlorosilane, phenyldi-n-propylchlorosilane, phenyldiisopropylchlorosilane, phenyldi-n-butylchlorosilane, phenyldiisobutylchlorosilane, phenyldi-sec-butylchlorosilane, phenyldi-tert-butylchlorosilane, phenyldi-n-octylchlorosilane, phenyldicyclopentylchlorosilane, phenyldicyclohexylchlorosilane, phenyldimethallylchlorosilane, phenyldi-o-tolylchlorosilane, phenyldi-2,3-xylylchlorosilane, phenyldi-2,4-xylylchlorosilane, phenyldi-2,5-xylylchlorosilane, phenyldi-2,6-xylylchlorosilane, phenyldi-3,4-xylylchlorosilane, phenyldi-3,5-xylylchlorosilane, phenyldimesitylchlorosilane, n-propyldimethylchlorosilane, isopropyldimethylchlorosilane, n-butyldimethylchlorosilane, isobutyldimethylchlorosilane, sec-butyldimethylchlorosilane, tert-butyldimethylchlorosilane, n-octyldimethylchlorosilane, cyclopentyldimethylchlorosilane, cyclohexyldimethylchlorosilane, methallyldimethylchlorosilane, o-tolyldimethlychlorosilane, 2,3-xylyldimethylchlorosilane, 2,4-xylyldimethylchlorosilane, 2,5-xylyldimethylchlorosilane, 2,6-xylyldimethylchlorosilane, 3,4-xylyldimethylchlorosilane, 3,5-xylyldimethylchlorosilane, mesityldimethylchlorosilane, n-propylvinylmethylchlorosilane, isopropylvinylmethylchlorosilane, n-butylvinylmethylchlorosilane, isobutylvinylmethylchlorosilane, sec-butylvinylmethylchlorosilane, tert-butylvinylmethylchlorosilane, n-octylvinylmethylchlorosilane, cyclopentylvinylmethylchlorosilane, cyclohexylvinylmethylchlorosilane, methallylvinylmethylchlorosilane, o-tolylvinylmethylchlorosilane, 2,3-xylylvinylmethylchlorosilane, 2,4-xylylvinylmethylchlorosilane, 2,5-xylylvinylmethylchlorosilane, 2,6-xylylvinylmethylchlorosilane, 3,4-xylylvinylmethylchlorosilane, 3,5-xylylvinylmethylchlorosilane, mesitylvinylmethylchlorosilane, n-propylphenylmethylchlorosilane, isopropylphenylmethylchlorosilane, n-butylphenylmethylchlorosilane, isobutylphenylmethylchlorosilane, sec-butylphenylmethylchlorosilane, tert-butylphenylmethylchlorosilane, n-octylphenylmethylchlorosilane, cyclopentylphenylmethylchlorosilane, cyclohexylphenylmethylchlorosilane, methallylphenylmethylchlorosilane, o-tolylphenylmethylchlorosilane, 2,3-xylylphenylmethylchlorosilane, 2,4-xylylphenylmethylchlorosilane, 2,5-xylylphenylmethylchlorosilane, 2,6-xylylphenylmethylchlorosilane, 3,4-xylylphenylmethylchlorosilane, 3,5-xylylphenylmethylchlorosilane, mesitylphenylmethylchlorosilane, n-propyldivinylchlorosilane, isopropyldivinylchlorosilane, n-butyldivinylchlorosilane, isobutyldivinylchlorosilane, sec-butyldivinylchlorosilane, tert-butyldivinyl chlorosilane, n-octyldivinylchlorosilane, cyclopentyldivinylchlorosilane, cyclohexyldivinylchlorosilane, methallyldivinylchlorosilane, o-tolyldivinylchlorosilane, 2,3-xylyldivinylchlorosilane, 2,4-xylyldivinylchlorosilane, 2,5-xylyldivinylchlorosilane, 2,6-xylyldivinylchlorosilane, 3,4-xylyldivinylchlorosilane, 3,5-xylyldivinylchlorosilane, mesityldivinylchlorosilane, n-propyldiphenylchlorosilane, isopropyldiphenylchlorosilane, n-butyldiphenylchlorosilane, isobutyldiphenylchlorosilane, sec-butyldiphenylchlorosilane, tert-butyldiphenylchlorosilane, n-octyldiphenylchlorosilane, cyclopentyldiphenylchlorosilane, cyclohexyldiphenylchlorosilane, methallyldiphenylchlorosilane, o-tolyldiphenylchlorosilane, 2,3-xylyldiphenylchlorosilane, 2,4-xylyldiphenylchlorosilane, 2,5-xylyldiphenylchlorosilane, 2,6-xylyldiphenylchlorosilane, 3,4-xylyldiphenylchlorosilane, 3,5-xylyldiphenylchlorosilane, mesityldiphenylchlorosilane, etc., but these particular examples do not limit the scope of the intended tri-organo-monochlorosilane.

Among the compound exemplified above which may be produced by the third aspect process of this invention, triisopropylchlorosilane, tri-sec-butylchlorosilane, tricyclopentylchlorosilane, tricyclohexylchlorosilane and tertbutyldimethylchlorosilane are particularly useful for the purpose of the production of medicines and others and are also useful as a tri-organo-chlorosilane which is a silylating agent to be used for protecting the functional groups of synthetic intermediates or is an intermediate for preparation of such silylating agent.

Several methods may be used for the preparation of a tri-organo-silane compound of the general formula (XIb)

$(R^1)(R^2)(R^{3a})SiZ^2$          (XIb)

which contains a bulky hydrocarbon group $R^{3a}$ such as a secondary or tertiary alkyl group, and which is used as a starting compound in the third aspect process of this invention.

To be concrete, there are available Method (A), Method (B), Method (C), Method (D), Method (E) and Method (F) as described in (i)-(vi) below.

(i) Method (A) is adapted for the preparation of a tri-organo-silane compound of the general formula (XIb)

$(R^1)(R^2)(R^{3a})SiZ^2$          (XIb)

where the group $Z^2$ in the general formula (XIb) does not mean the 2-substituted or unsubstituted-2-chloroethoxy group of the formula (A), which is to be used as the starting compound. This Method (A) comprises reacting tetrachlorosilane or a di or mono-organo-di or trichlorosilane of the general formula (XIII)

$(R^1)_x(R^2)_ySiCl_{4-(x+y)}$          (XIII)

wherein $R^1$ and $R^2$ have the same meanings as defined above and x and y each are an integer of 0, 1 or 2, and are to be within the range of $0 \leq (x+y) \leq 2$, with an alcohol of the general formula (XIV)

$R^6OH$          (XIV)

wherein $R^6$ stands for a primary or secondary alkyl group, a cycloalkyl group or an aralkyl group, thereby to produce an organo-unsubstituted or mono-organo or di-organo-mono (alkoxy, cycloalkyloxy or aralkyloxy)-tri, di or monochlorosilane of the general formula (XVa)

$$(R^1)_x(R^2)_y SiCl_{3-(x+y)}(OR^6) \quad (XVa)$$

wherein $R^1$, $R^2$, $R^6$, x and y have the same meanings as defined above, and then reacting the tri, di or monochlorosilane compound of the formula (XVa) with a Grignard reagent of the formula (XVI)

$$(R^{3a})MgX \quad (XVI)$$

wherein $R^{3a}$ stands for a secondary alkyl group, tertiary alkyl group or a cycloalkyl group as defined above, or $R^{3a}$ stands for an alkyl-substituted aromatic hydrocarbon group of which alkyl substituent is bonding to a carbon atom present in the aromatic hydrocarbon group, with said carbon atom being adjacent to the carbon atom of the aromatic hydrocarbon group that is bonding to the magnesium atom, and X stands for chlorine, bromine or iodine atom.

As preferred examples of the chlorosilane compound of the formula (XIII) to be used for this Method (A), there may be mentioned tetrachlorosilane, methyltrichlorosilane, dimethyldichlorosilane, ethyltrichlorosilane, vinyltrichlorosilane, divinyldichlorosilane, phenyltrichlorosilane, diphenyldichlorosilane, vinylmethyldichlorosilane, phenylmethyldichlorosilane, and others.

The alcohol $R^6OH$ of the formula (XIV) to be reacted with the chlorosilane compound of the formula (XIII) includes a primary or secondary alkyl alcohol or a cycloalkyl alcohol or an aralkyl alcohol.

Of the alcohol of the formula (XIV), the alkyl alcohol (an alkanol) may concretely be methanol, ethanol, n-propanol, isopropanol, n-butanol, isobutanol, sec-butanol, etc. The cycloalkyl alcohol may, for example, be cyclopentyl alcohol and cyclohexyl alcohol. The aralkyl alcohol may, for example, be benzyl alcohol, phenylethyl alcohol, etc.

The step of the alkoxylation or aralkyloxylation reaction comprising reacting tetrachlorosilane or an organo-chlorosilane of the formula (XIII) with an alcohol of the formula (XIV) may preferably be done by using 0.5-2 moles, particularly 0.5-1.5 moles, of the alcohol of the formula (XIV) per 1 mole of tetrachlorosilane or the organo-chlorosilane of the formula (XIII).

The step of the alkoxylation or aralkyloxylation reaction may be carried out in the absence of a solvent or in an aprotic organic solvent. As the aprotic organic solvent, there may be used either an ether solvent usually used in the Grignard reactions, such as diethylether, tetrahydrofuran, or a hydrocarbon solvent such as hexane, toluene. The solvent may be used singly or in combination of two or more. The alkoxylation or aralkyloxylation reaction may be effected at a temperature in the range of −10° C.-150° C., preferably 0° C.-100° C. This alkoxylation or aralkyloxylation reaction with the alcohol of the formula (XIV) generates hydrogen chloride gas as a by-product, and so it is necessary to expel the hydrogen chloride gas from the reaction system.

After the completion of the alkoxylation or aralkyloxylation reaction, there is obtained a reaction solution containing a mono(alkoxy, cycloalkyloxy or aralkyloxy)-chlorosilane of the formula (XVa) thus produced. The mono-organo-chlorosilane of the formula (XVa) may be separated or recovered by subjecting the reaction solution to a fractional distillation under an atmospheric pressure or a reduced pressure. Alternatively, the said reaction solution may be used as such, namely directly, in the subsequent Grignard reaction step.

Next, the mono(alkoxy, cycloalkyloxy or aralkyloxy)-chlorosilane of the formula (XVa) as obtained in the above step is reacted with a Grignard reagent of the general formula (XVI).

As concrete examples of the Grignard reagent of the formula (XVI), there may be enumerated isopropyl magnesium chloride, isopropyl magnesium bromide, isopropyl magnesium iodide; sec-butyl magnesium chloride, sec-butyl magnesium bromide, sec-butyl magnesium iodide; sec-pentyl magnesium chloride, sec-pentyl magnesium bromide and sec-pentyl magnesium iodide. Further examples of the Grignard reagent may include cyclopentyl magnesium chloride, cyclopentyl magnesium bromide, cyclopentyl magnesium iodide; cyclohexyl magnesium chloride, cyclohexyl magnesium bromide, cyclohexyl magnesium iodide; tert-butyl magnesium chloride, tert-butyl magnesium bromide, tert-butyl magnesium iodide; 1,1-dimethylpropyl magnesium chloride, 1,1-dimethylpropyl magnesium bromide, 1,1-dimethylpropyl magnesium iodide; 1-methyl-1-ethylpropyl magnesium chloride, 1-methyl-1-ethylpropyl magnesium bromide, 1-methyl-1-ethylpropyl magnesium iodide; 1,1-diethylpropyl magnesium chloride, 1,1-diethylpropyl magnesium bromide, 1,1-diethylpropyl magnesium iodide; 1,1,2-trimethylpropyl magnesium chloride, 1,1,2-trimethylpropyl magnesium bromide, 1,1,2-trimethylpropyl magnesium iodide; 1-methylcyclopentyl magnesium chloride, 1-methylcyclopentyl magnesium bromide, 1-methylcyclopentyl magnesium iodide; 1-methylcyclohexyl magnesium chloride, 1-methylcyclohexyl magnesium bromide, 1-methylcyclohexyl magnesium iodide; 1-ethylcyclohexyl magnesium chloride, 1-ethylcyclohexyl magnesium bromide, 1-ethylcyclohexyl magnesium iodide; o-tolyl magnesium chloride, o-tolyl magnesium bromide, o-tolyl magnesium iodide; 2,3-xylyl magnesium chloride, 2,3-xylyl magnesium bromide, 2,3-xylyl magnesium iodide; 2,4-xylyl magnesium chloride, 2,4-xylyl magnesium bromide, 2,4-xylyl magnesium iodide; 2,5-xylyl magnesium chloride, 2,5-xylyl magnesium bromide, 2,5-xylyl magnesium iodide; 2,6-xylyl magnesium chloride, 2,6-xylyl magnesium bromide, 2,6-xylyl magnesium iodide; mesityl magnesium chloride, mesityl magnesium bromide, mesityl magnesium iodide; 1-naphthyl magnesium chloride, 1-naphthyl magnesium bromide or 1-naphthyl magnesium iodide. However, these examples do not limit the scope of the usable Grignard reagent.

The Grignard reaction above may be carried out in an ether solvent or in a mixed solvent of an ether solvent with an aprotic organic solvent. As the usable aprotic organic solvent, there may be mentioned a hydrocarbon solvent such as hexane, heptane, toluene, xylene, etc. The Grignard reagent of the formula (XVI) may preferably be used for the intended reaction in a proportion of 1-10 moles, preferably 1-5 moles per 1 mole of the mono(alkoxy, cycloalkyloxy or aralkyloxy)-chlorosilane of the formula (XVa). When the reaction solution as obtained in the preceding reaction step for the preparation of the compound of the formula (XVa) is used as such in the step of the Grignard reaction, it is usually desirable that the said Grignard reaction is carried out, if the solvent is used for the Grignard reaction, in the ether solvent or the mixed solvent of the ether solvent with the aprotic solvent which is same as that used in the preceding reaction step. The Grignard reaction may be conducted at a temperature in the range of −10° C.-150° C., preferably 20° C.-150° C. Further, this reaction is desirably carried out under an inert gas atmosphere such as nitrogen, argon, etc., because the presence of oxygen in the reaction system may cause undesirable reaction of the Grignard reagent with oxygen, thus bringing about a decrease in the yield of the desired product.

The Grignard reaction may be carried out in a usual manner for 1-24 hours up to the completion. Thereafter, the resulting reaction mixture or solution is mixed with a suitable amount of a saturated aqueous ammonium chloride solution or a dilute sulfuric acid, so that the inorganic magnesium salt as deposited in the reaction mixture can be dissolved in said aqueous ammonium chloride solution or the dilute sulfuric acid. The organic layer may then be separated from the aqueous layer and subjected to a fractional distillation under an atmospheric or reduced pressure, so that there can be separated and recovered the fraction consisting of the desired tri-organo-mono(alkoxy, cycloalkyloxy or aralkyloxy)silane of the general formula (XIb).

(ii) Method (B) is adapted for the preparation of an organo-unsubstituted or mono or di-organo-mono(2-substituted-2-chloroethoxy)silane of the formula (XIb-1)

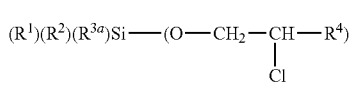
(XIb-1)

wherein $R^1$, $R^2$, $R^{3a}$ and $R^4$ have the same meanings as defined above, which is included within the scope of the tri-organo-silane compound of the general formula (XIb)

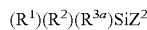
(XIb)

which is to be used as a starting compound. This Method (B) comprises reacting tetrachlorosilane or a di or mono-organo-di or trichlorosilane formula (XIII)

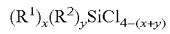
(XIII)

wherein $R^1$ and $R^2$ have the same meanings as defined above and x and y are the integer as defined above, with an alkylene oxide or a glycidylether of the formula (XVII)

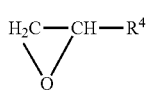
(XVII)

wherein $R^4$ is a hydrogen atom or an alkyl group of 1-8 carbon atoms, or $R^4$ is an alkoxymethylene group, an alkenyloxymethylene group or an aryloxymethylene group of the formula —$CH_2$—O—$R^5$ where $R^5$ is a straight or branched chain alkyl group of 1-20 carbon atoms or an alkenyl group of 2-10 carbon atoms or an aryl group, thereby to produce an organo-unsubstituted or mono-organo or di-organo-mono(2-substituted or unsubstituted-2-chloroethoxy)-tri, di or monochlorosilane of the formula (XVb)

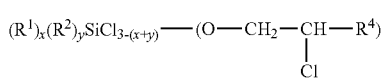
(XVb)

wherein $R^1$, $R^2$, $R^4$, x and y have the same meanings as defined above, and then reacting the chlorosilane compound of the formula (XVb) with a Grignard reagent of the formula (XVI)

(XVI)

wherein $R^{3a}$ stands for a secondary alkyl group, a tertiary alkyl group or a cycloalkyl group as defined above, or $R^{3a}$ is an alkyl-substituted aromatic hydrocarbon group as defined above.

In case where the group $R^4$ of the compound of the formula (XVII) used in Method (B) is a hydrogen atom or an alkyl group, the alkylene oxide of the formula (XVII) is an epoxy compound having an epoxy group at the end thereof, such as ethylene oxide, propylene oxide, and the like.

In case where the group $R^4$ of the compound of the formula (XVII) is an alkoxymethylene group or an aryloxymethylene group, the compound of the formula (XVII) is a glycidylether, such as butylglycidylether, glycidylmethylether, etc. Another examples of the glycidylether of the formula (XVII) are 2-ethylhexylglycidylether, octadecylglycidylether, allylglycidylether and glycidylphenylether.

In Method (B), the reaction can proceed by reacting 0.5-2 moles of an alkylene oxide or a glycidylether of the general formula (XVII) with 1 mole of tetrachlorosilane or an organo-chlorosilane of the formula (XIII) in the absence of a solvent or in an aprotic organic solvent, for example, diethylether at a temperature of −10° C.-150° C. Hydrocarbon solvent may be used as a co-solvent. In contrast to Method (A), no hydrogen chloride gas is generated in Method (B), because the epoxy group of the compound of the formula (XVII) can be ring-opened upon the reaction with the chlorosilane of the formula (XIII), whereby to uptake therein the chloro group of the chlorosilane compound of the formula (XIII).

(iii) Method (C) is adapted for the preparation of a tri-organo-silane compound of the formula (XIb) where the group $Z^2$ in the formula (XIb) does not mean the 2-substituted or unsubstituted-2-chloroethoxy group of the formula (A). This Method (C) comprises adding to tetrachlorosilane or a di or mono-organo-di or trichlorosilane of the formula (XIII)

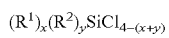
(XIII)

wherein $R^1$ and $R^2$ have the same meanings as defined above and x and y are the integer as defined above, an alkoxysilane of the formula (XIX)

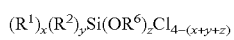
(XIX)

wherein $R^1$, $R^2$ and $R^6$ have the same meanings as defined above, x and y each stand for an integer of 0, 1 or 2, but are to be within the range of $0 \leq (x+y) \leq 2$, and z stands for an integer of 2, 3 or 4, but is to be within the range of $2 \leq (x+y+z) \leq 4$, then effecting a disproportionation reaction between the chlorosilane of the formula (XIII) and the alkoxysilane of the formula (XIX) to produce an alkoxychlorosilane, and further reacting the resulting alkoxychlorosilane product with a Grignard reagent of the formula (XVI), $(R^{3a})MgX$.

The groups $R^1$ and $R^2$ of the alkoxysilane of the formula (XIX) used for Method (C) stand for the same substituents as $R^1$ and $R^2$ of the formula (XIa) or (XIII). Concrete examples of the alkoxysilane of the formula (XIX) may be tetramethoxysilane, tetraethoxysilane, methyltrimethoxysilane, methyltriethoxysilane, dimethyldimethoxysilane, dimethyldiethoxysilane, vinyltrimethoxysilane, vinyltriethoxysilane, divinyldimethoxysilane, divinyldiethoxysilane, phenyltrimethoxysilane, phenyltriethoxysilane, diphenyldimethoxysilane, diphenyldiethoxysilane, vinylmethyldimethoxysilane, vinylmethyldiethoxysilane, phenylmethyldimethoxysilane, phenylmethyldiethoxysilane, and the like.

In the disproportionation reaction as effected in Method (C), the chlorosilane of the formula (XIII) and the alkoxysilane of the formula (XIX) are preferably reacted together in such a manner that 0.1-3 moles, particularly 0.2-1.5 moles of the alkoxysilanes of the formula (XIX) are used per 1 mole of the chlorosilane of the formula (XIII), so as to make the proportion of the desired alkoxychlorosilane product to be produced at a maximum. The disproportionation reaction may be conducted in the absence of a solvent at a temperature of 0° C.-50° C., preferably 10° C.-30° C.

The reaction solution resulting from the disproportionation reaction step as above is in the form of a solution of mixed products which contains not only the desired organo-unsubstituted or mono or di-organo-mono(alkoxy or cycloalkyloxy or aralkyloxy)-tri, di or monochlorosilane compound as the main component, but also contains the starting materials yet unreacted and some by-products formed by side-reactions, in which two or more of the chloro groups of the starting chlorosilane compound (XIII) have been alkoxylated. The organo-chlorosilane product is then subjected to a Grignard reaction with a Grignard reagent (XVI) in a next step. In this next step of Grignard reaction, the reaction solution resulted from the preceding disproportionation reaction step can be used as such. Otherwise, the said reaction solution is subjected to fractional distillation to isolate therefrom the desired mono(alkoxy or cycloalkyloxy or aralkyloxy)silane as a purified product, which is then used for the next Grignard reaction step.

(iv) Method (D) is adapted for the preparation of a tri-organosilane compound of the general formula (XIb)

$(R^1)(R^2)(R^{3a})SiZ^2$ (XIb)

which is to be used as the starting compound. The Method (D) comprises adding an alcohol of the formula (XIV)

$(R^6)OH$ (XIV)

wherein $R^6$ is a primary or secondary alkyl group, a cycloalkyl group or an aralkyl group as defined above, or an alkylene oxide or a glycidylether of the formula (XVII)

(XVII)

wherein $R^4$ is a hydrogen atom or an alkyl group of 1-8 carbon atoms as shown above, or $R^4$ is an alkoxymethylene group, an alkenyloxymethylene group or an aryloxymethylene group of the formula —CH$_2$—O—R$^5$ where $R^5$ is a straight or branched chain alkyl group of 1-20 carbon atoms or an alkenyl group of 2-10 carbon atoms or an aryl group, to a Grignard reagent of the formula (XVI)

$(R^{3a})MgX$ (XVI)

wherein $R^{3a}$ stands for a secondary alkyl group, a tertiary alkyl group or a cycloalkyl group, or $R^{3a}$ stands for an alkyl-substituted aromatic hydrocarbon group of which said alkyl substituent is bonding to a carbon atom present in the aromatic hydrocarbon group, with said carbon atom being adjacent to the carbon atom of the aromatic hydrocarbon group that is bonding to the magnesium atom, then effecting the Grignard reaction therebetween, then adding to the solution formed of the resulting Grignard reaction mixture an amount of tetrachlorosilane or a di or mono-organo-di or trichlorosilane of the formula (XIII)

$(R^1)_x(R^2)_y SiCl_{4-(x+y)}$ (XIII)

wherein $R^1$ and $R^2$, as defined in the formula (XI), are equal to each other or are different from each other and each stand for a primary, secondary or tertiary alkyl group, a cycloalkyl group, an alkenyl group, an alkynyl group, an aralkyl group or an aryl group and x and y each stand for an integer of 0, 1 or 2, but are to be within the range of $0 \leq (x+y) \leq 2$, then effecting the reactions between the reactive components, and then separating and recovering from the resulting reaction solution containing the different reaction products, the desired tri-organo-silane compound of the formula (XIb) above.

(v) Method (E) is adapted for the preparation of the starting tri-organo-silane compound of the formula (XIb)

$(R^1)(R^2)(R^{3a})SiZ^2$ (XIb)

Method (E) comprises the steps of adding to the Grignard reagent of the formula (XVI) as used in Method (D) above an amount of tetrachlorosilane or a di or mono-organo-di or trichlorosilane of the general formula (XIII) as used in Method (D) above, reacting them with each other and subsequently adding to the so obtained reaction mixture an amount of the alcohol of the formula (XIV) or the alkylene oxide or glycidylether of the formula (XVII) as used in Method (D), then reacting the reactive components with each other, and finally recovering the desired tri-organo-silane compound of the formula (XIb) from the resulting different reaction products so formed.

The silane compound of the formula (XIa) or (XIb) as prepared by Method (A) to Method (E) mentioned above may be the one which has been isolated from the reaction solution obtained in their preparation step, or may be the one which still remains contained in such reaction solution unpurified.

(vi) Method (F) is adapted for the preparation of a starting tri-organo-silane compound of the formula (XIa)

$(R^1)(R^2)(R^3)SiZ^1$ (XIa)

Method (F) comprises reacting a tri-organo-hydrosilane compound of the formula (XVIII)

$(R^1)(R^2)(R^3)SiH$ (XVIII)

wherein $R^1$, $R^2$ and $R^3$ are the same as or different from each other and each are a primary, secondary or tertiary alkyl group, a cycloalkyl group, an alkenyl group, an alkynyl group, an aralkyl group or an aryl group, and wherein all the groups $R^1$, $R^2$ and $R^3$ are not methyl group simultaneously, with an alcohol of the formula (XIV)

$R^6OH$ (XIV)

wherein $R^6$ stands for a primary or secondary alkyl group, a cycloalkyl group or an aralkyl group as defined above, in the presence of an alkaline catalyst. By Method (F) above, there can be produced a tri-organo-mono(alkoxy, cycloalkyloxy or alkenyloxy)silane of the formula (XIa-1)

$(R^1)(R^2)(R^3)Si(OR^6)$ (XIa-1)

wherein $R^1$, $R^2$, $R^3$ and $R^6$ have the same meanings as defined above.

In Method (F) above, the alkaline catalyst used may be an alkali metal hydroxide such as sodium hydroxide and potassium hydroxide, or a sodium alcoholate of a lower alkanol such as sodium methylate and sodium ethylate. The reaction of the tri-organo-hydrosilane of the formula (XVIII) with the alcohol of the formula (XIV) may be conducted in an alkanol solvent such as methanol or ethanol. The reaction may be effected at a temperature from 20° C. to the refluxing temperature.

In case where the tri-organo-silane compound of the formula (XIa) to be used as a starting compound for the process according to the third aspect of this invention has a hydrolyzable group $Z^1$, the tri-organosilane compound (XIa) having such group $Z^1$ may be prepared by a process of synthesis using an alkyl orthosilicate and a Grignard reagent (see a Japanese book titled "Organic Silicon Chemistry", p. 95 and p. 242, edited jointly by Makoto Kumada and Rokuro Okawara) or by a process for synthesis of sulfate esters (see the book titled "Organic Silicon Chemistry", p. 291, edited jointly by Makoto Kumada and Rokuro Okawara), or by a process for synthesis of amino, cyano, isocyano and isocyanato-silanes (see the book titled "Organic Silicon Chemistry", edited jointly by Makoto Kumada and Rokuro Okawara).

According to the third aspect process of this invention, it is possible to produce a tri-organo-monochlorosilane containing the bulky hydrocarbon groups, by simple and convenient reaction procedures and in good yield.

As mentioned above, the processes according to the first and second aspects of this invention are now provided for the purpose of producing the tri-organo-monoalkoxysilanes.

Apart from the processes of the first and second aspects of this invention, we now have also proceeded our further investigations for the purpose of developing a new process capable of producing a tri-organo-monoalkoxysilane containing the bulky hydrocarbon group or groups such as a secondary alkyl group, a tertiary alkyl group, a cycloalkyl group or an aryl group, by easy and safe reaction procedures.

As a result of our eager investigations made, we have now found that, when the chlorosilane of the above formula (I) to be used as the starting compound is subjected to a reaction with the Grignard reagent of the above formula (II), and when a co-presence of an alcohol of the formula (XXIII) defined below or an epoxy compound of the formula (XXIV) defined below is provided in the reaction system of conducting such reaction, there can progress the reaction of said alcohol or epoxide compound with the Grignard reagent of the formula (II) to produce a magnesium alkoxide compound as an intermediate product, and said intermediate product can then react with one of the chloro groups of the starting chlorosilane of the formula (I), thereby to produce a monoalkoxy-chlorosilane, with involving such advantage that the reactivity of the remaining chloro groups in the resulting monoalkoxy-chlorosilane as produced has been enhanced, and we have found that said monoalkoxychlorosilane as produced can then easily react further with the Grignard reagent containing the secondary alkyl group, tertiary alkyl group, cycloalkyl group or alkyl-substituted aromatic hydrocarbon group which is of a high steric hindrance in nature, whereby such secondary alkyl group, tertiary alkyl group or cycloalkyl group or alkyl-substituted aromatic hydrocarbon group can be introduced onto the silicon atom of the monoalkoxychlorosilane. On the basis of this finding, we have accomplished a fourth aspect of this invention as described below.

According to the fourth aspect of this invention, there is provided a process for the production of a tri-organo-mono (alkoxy, cycloalkyloxy or aralkyloxy)-silane containing a bulky hydrocarbon group or groups R therein and having the formula (XXVa)

  (XXVa)

wherein $R^1$ stands for a primary, secondary or tertiary alkyl group, a cycloalkyl group, an alkenyl group, an alkynyl group, an aryl group or an aralkyl group, $R^2$ stands for a secondary alkyl group, a tertiary alkyl group, a cycloalkyl group or an aryl group, and wherein R stands for a secondary alkyl group or a tertiary alkyl group or a cycloalkyl group, or R stands for an alkyl-substituted aromatic hydrocarbon group as defined below, and $R^7$ has the same meaning as $R^3$ defined below, or $R^7$ is a group of the formula —$CH_2$—CH(R)—$R^4$ where R and $R^4$ have the same meaning as defined below, and x stands for an integer of 0 or 1 and y stands for an integer of 0, 1 or 2, where the integers for x and y are to be within the range of $0 \leq (x+y) \leq 2$, characterized in that the process comprises reacting tetrachlorosilane or a di or mono-organo-di or trichlorosilane of the formula (XXI)

  (XXI)

wherein $R^1$ and $R^2$ have the same meanings as defined above and x and y each stand for an integer as defined above, with a Grignard reagent of the formula (XXII)

RMgX  (XXII)

wherein R stands for a secondary alkyl group or a tertiary alkyl group or a cycloalkyl group, or R stands for an alkyl-substituted aromatic hydrocarbon group of which the alkyl substituent is bonding to a carbon atom present in the aromatic hydrocarbon group, with said carbon atom being adjacent to the carbon atom of the aromatic hydrocarbon group that is bonding to the magnesium atom, and X stands for a chlorine, bromine or iodine atom, in a manner such that the reaction of tetrachlorosilane or the di or trichlorosilane of the formula (XXI) with the Grignard reagent of the formula (XXII) is effected with addition of and reaction with an alcohol of the formula (XXIII)

$R^3OH$  (XXIII)

wherein $R^3$ stands for a primary or secondary alkyl group, a cycloalkyl group or an aralkyl group, or an alkylene oxide or a glycidylether of the formula (XXIV)

  (XXIV)

wherein $R^4$ stands for a hydrogen atom or an alkyl group of 1-8 carbon atoms, or $R^4$ stands for an alkoxymethylene group, an alkenyloxymethylene group or an aryloxymethylene group of the formula —$CH_2$—O—$R^5$ where $R^5$ is a straight or branched chain alkyl group of 1-20 carbon atoms, an alkenyl group of 2-10 carbon atoms or an aryl group.

In tetrachlorosilane or the di or mono-organo-di or trichlorosilane of the formula (XXI)

  (XXI)

which is to be used in the fourth aspect process of this invention, $R^1$ stands for a primary, secondary or tertiary alkyl group, a cycloalkyl group, an alkenyl group, an alkynyl group, an aryl group or an aralkyl group and $R^2$ stands for a secondary alkyl group, a tertiary alkyl group, a cycloalkyl group or an aryl group as shown above.

The primary, secondary or tertiary alkyl group for the substituent $R^1$ in the chlorosilane compound of the formula (XXI) above is preferably a straight or branched chain alkyl group of 1-10 carbon atoms, and concrete examples thereof may include methyl group, ethyl group, n-propyl group, isopropyl group, n-butyl group, isobutyl group, sec-butyl group, tert-butyl group, n-pentyl group, isopentyl group, sec-pentyl group, 1,1-dimethylpropyl group, n-hexyl group, n-heptyl group, n-octyl group, 2-ethylhexyl group, n-dodecyl group and n-octadecyl group. The cycloalkyl group for $R^1$ may be those of 3-8 carbon atoms such as cyclopentyl group and cyclohexyl group.

As the alkenyl group for $R^1$ in the formula (XXI), there may be exemplified vinyl group, methallyl group, allyl group and the like. As the alkynyl group for $R^1$, there are ethynyl group, 1-propynyl group and the like. As the aryl group for $R^1$, there are, for example, phenyl group, an alkyl-substituted phenyl group such as o-tolyl group, m-tolyl group, p-tolyl group, 2,3-xylyl group, 2,4-xylyl group, 2,5-xylyl group, 2,6-xylyl group, 3,4-xylyl group, 3,5-xylyl group, mesityl group, or 1-naphthyl group, and the like. As the aralkyl group for $R^1$, there are mentioned a lower alkyl group substituted with phenyl group, such as benzyl group, phenylethyl group (i.e. phenethyl group) and the like.

The secondary alkyl group for $R^2$ in the formula (XXI) is those of 3-10 carbon atoms, examples of which may include isopropyl group, sec-butyl group, sec-pentyl group and the like. The tertiary alkyl group for $R^2$ is those of 4-10 carbon atoms, examples of which may include tert-butyl group, 1,1-dimethylpropyl group, 1-ethyl-1-methylpropyl group, 1,1,2-trimethylpropyl group and 1,1-diethylpropyl group.

The cycloalkyl group for $R^2$ in the formula (XXI) may be those of 3-8 carbon atoms such as cyclopentyl group and cyclohexyl group. The aryl group for $R^2$ may be the same as those exemplified as $R^1$ above.

As preferred examples of the chlorosilane compound of the formula (XXI), there are mentioned tetrachlorosilane, methyltrichlorosilane, ethyltrichlorosilane, vinyltrichlorosilane, phenyltrichlorosilane, diphenyldichlorosilane, phenylmethyldichlorosilane and the like.

In the organo-metallic compound RMgX which is to be used as the Grignard reagent of the formula (XII) in the fourth aspect process of this invention, the bulky hydrocarbon group R contained therein is a secondary or tertiary alkyl group or a cycloalkyl group, or an alkyl-substituted aromatic hydrocarbon group. Examples of the secondary alkyl group for R may include isopropyl group, sec-butyl group, sec-pentyl group and the like. Examples of the tertiary alkyl group for R may include tert-butyl group, 1,1-dimethylpropyl group, 1-methyl-1-ethylpropyl group, 1,1-diethylpropyl group, 1,1,2-trimethylpropyl group and the like. As the cycloalkyl group, there are exemplified cyclopentyl group, cyclohexyl group, 1-methylcyclopentyl group, 1-methylcyclohexyl group, 1-ethylcyclohexyl group and the like.

As the alkyl-substituted aromatic hydrocarbon group for R, there are exemplified an alkyl-substituted phenyl group such as o-tolyl group, 2,3-xylyl group, 2,4-xylyl group, 2,5-xylyl group, 2,6-xylyl group, mesityl group or 1-naphthyl group and the like. The group X stands for a halogen group being chlorine, bromine or iodine.

As concrete examples of the Grignard reagent of the formula (XXII), there may be enumerated isopropyl magnesium chloride, isopropyl magnesium bromide, isopropyl magnesium iodide; sec-butyl magnesium chloride, sec-butyl magnesium bromide, sec-butyl magnesium iodide; sec-pentyl magnesium chloride, sec-pentyl magnesium bromide, sec-pentyl magnesium iodide; and cyclopentyl magnesium chloride, cyclopentyl magnesium bromide, cyclopentyl magnesium iodide; cyclohexyl magnesium chloride, cyclohexyl magnesium bromide, cyclohexylmagnesium iodide; tert-butyl magnesium chloride, tert-butyl magnesium bromide, tert-butyl magnesium iodide; 1,1-dimethylpropyl magnesium chloride, 1,1-dimethylpropyl magnesium bromide, 1,1-dimethylpropyl magnesium iodide; 1-methyl-1-ethylpropyl magnesium chloride, 1-methyl-1-ethylpropyl magnesium bromide, 1-methyl-1-ethylpropyl magnesium iodide; 1,1-diethylpropyl magnesium chloride, 1,1-diethylpropyl magnesium bromide, 1,1-di-ethylpropyl magnesium iodide; and 1,1,2-trimethylpropyl magnesium chloride, 1,1,2-trimethylpropyl magnesium bromide, 1,1,2-trimethylpropyl magnesium iodide; and 1-methylcyclopentyl magnesium chloride, 1-methyl-cyclopentyl magnesium bromide, 1-methylcyclopentyl magnesium iodide; 1-methylcyclohexyl magnesium chloride, 1-methylcyclohexyl magnesium bromide, 1-methylcyclohexyl magnesium iodide; 1-ethylcyclohexyl magnesium chloride, 1-ethylcyclohexyl magnesium bromide, 1-ethylcyclohexyl magnesium iodide; and o-tolyl magnesium chloride, o-tolyl magnesium bromide, o-tolyl magnesium iodide; 2,3-xylyl magnesium chloride, 2,3-xylyl magnesium bromide, 2,3-xylyl magnesium iodide; 2,4-xylyl magnesium chloride, 2,4-xylyl magnesium bromide, 2,4-xylyl magnesium iodide; 2,5-xylyl magnesium chloride, 2,5-xylyl magnesium bromide, 2,5-xylyl magnesium iodide; 2,6-xylyl magnesium chloride, 2,6-xylyl magnesium bromide, 2,6-xylyl magnesium iodide; mesityl magnesium chloride, mesityl magnesium bromide, mesityl magnesium iodide; 1-naphthyl magnesium chloride, 1-naphthyl magnesium bromide and 1-naphthyl magnesium iodide, but these particular examples do not limit the scope of the usable Grignard reagent.

The alcohol $R^3OH$ of the formula (XXIII) to be used in the fourth aspect process of this invention is a primary or secondary alkylalcohol or a cycloalkylalcohol or an aralkylalcohol.

Of the alcohol of the formula (XXIII), the alkylalcohol (alkanol) may typically be methanol, ethanol, n-propanol, isopropanol, n-butanol, isobutanol, sec-butanol and the like. The cycloalkyl alcohol may typically be cyclopentyl alcohol and cyclohexyl alcohol, and the aralkyl alcohol may typically be benzyl alcohol, phenylethyl alcohol and the like.

Further, in respect of the alkylene oxide or glycidylether (i.e. epoxy compound as above) which may be used according to the fourth aspect process of this invention and which is of the formula (XXIV)

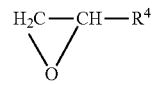

(XXIV)

wherein $R^4$ is a hydrogen atom or an alkyl group of 1-8 carbon atoms, or $R^4$ stands for an alkoxymethylene group, an alkenyloxymethylene group or an aryloxymethylene group of the formula $—CH_2—O—R^5$ where $R^5$ is a straight or branched chain alkyl group of 1-20 carbon atoms or an alkenyl group of 2-10 carbon atoms or an aryl group, said compound of the formula (XXIV) is an alkylene oxide, when $R^4$ is a hydrogen atom or an alkyl group, namely an epoxy compound having an epoxy group at the end thereof. The alkylene oxide may be ethylene oxide, propylene oxide and the like.

On the other hand, when $R^4$ of the epoxy compound of the formula (XXIV) is an alkoxymethylene group, an alkenyloxymethylene group or an aryloxymethylene group, said epoxy compound of the formula (XXIV) is a glycidylether. Examples of the glycidylether may be butylglycidylether, glycidylmethylether and the like. Further examples of the glycidylether may include 2-ethylhexylglycidylether, octadecylglycidylether; allylglycidylether; and glycidylphenylether.

As mentioned above, the process according to the fourth aspect of this invention comprises effecting the reaction of the chlorosilane compound of the formula (XXI) with the Grignard reagent of the formula (XXII), in a manner such that said reaction is carried out with making addition of the alcohol of the formula (XXIII) or the epoxy compound of the formula (XXIV) (more concretely an alkylene oxide or a glycidyl ether) upon starting such reaction, so that the alcohol (XXIII)

or the epoxy compound (XXIV) will participate in the reactions with the Grignard reagent and said chlorosilane compound.

The fourth aspect process of this invention may be carried out in accordance with Procedure (A) or Procedure (B) as explained in (i)-(ii) below, respectively.

(i) In Procedure (A), the reaction of the chlorosilane of the formula (XXI) with the Grignard reagent of the formula (XXII) is effected by admixing and reacting the Grignard reagent of the formula (XXXII) with the alcohol of the formula (XXIII) or the alkylene oxide or glycidylether of the formula (XXIV), then adding to the so obtained reaction mixture containing therein the remaining Grignard reagent and the resulting reaction product of the reaction of the Grignard reagent with the alcohol or the alkylene oxide or glycidylether an amount of tetrachlorosilane or a di or mono-organo-di or trichlorosilane of the formula (XXI), and effecting further reactions between the Grignard reagent, said reaction product and the added tetrachlorosilane or the added di or mono-organo-di or trichlorosilane present in the resultant mixture, to produce the tri-organo-mono-(alkoxy, cycloalkyloxy or aralkyloxy)silane of formula (XXVa). In this procedure (A), it is preferable to use and add 0.5-2 moles, particularly 0.5-1.5 moles of the alcohol of the formula (XXIII) or the epoxy compound of the formula (XXIV) per 1 mole of the chlorosilane compound of the formula (XXI) for effecting the reaction. It is also preferable that the Grignard reagent of the formula (XXII) is used in a proportion of 1-10 moles, particularly 2-5 moles per 1 mole of the chlorosilane compound of the formula (XXI) for effecting the reaction.

As mentioned above, in Procedure (A), the reaction is at first effected by admixing and reacting at first the Grignard reagent of the formula (XXII) with the alcohol of the formula (XXIII) or the epoxy compound of the formula (XXIV) (i.e. alkylene oxide or glycidylether). The so obtained reaction mixture or solution contains, as an intermediate reaction product, an alkoxy-, cycloalkyloxy- or aralkyloxy-magnesium halide of the formula (XXVIa)

$$(R^3O)MgX \quad (XXVIa)$$

wherein $R^3$ and X have the same meanings as defined above, which has been formed by the reaction of the Grignard reagent of the formula (XXII) with the alcohol of the formula (XXIII), or alternatively the said reaction mixture or solution contains a 2-substituted-ethoxy-magnesium halide of the formula (XXVIb)

(XXVIb)

wherein R, $R^4$ and X have the same meanings as defined above, which has been formed by the reaction of the Grignard reagent of the formula (XXII) with the epoxy compound of the formula (XXIV).

The above alkoxy-substituted magnesium halide compound of the formula (XXVIa) or the formula (XXVIb), which has thus been produced as the intermediate reaction product, is further reacted with the chlorosilane compound of the formula (XXI) to produce an intermediate chlorosilane derivative which is formed by the replacement of one of the chloro group of said chlorosilane compound (XXI) by the group $R^3O$— or the group $R^4$—CHR—$CH_2$—O— present in the formula (XXVIa) or (XXVIb).

Said intermediate chlorosilane derivative thus produced may be either an organo-unsubstituted or mono or di-organo-mono(alkoxy, cycloalkyloxy or aralkyloxy)-tri, di or monochlorosilane of the formula (XXVIIa)

$$(R^1)_x(R^2)_y SiCl_{3-(x+y)}(OR^3) \quad (XXVIIa)$$

wherein $R^1$, $R^2$, $R^3$, x and y have the same meanings as defined above, or an organo-unsubstituted or mono or di-organo-mono(2-substituted-ethoxy)-tri, di or monochlorosilane of the formula (XXVIIb)

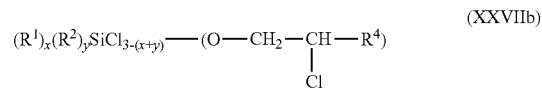
(XXVIIb)

wherein R, $R^1$, $R^2$, $R^4$, x and y have the same meanings as defined above.

The remaining chloro group or groups of the resulting tri, di or monochlorosilane derivative of the above formula (XXVIIa) or (XXVIIb) once produced as the above intermediate product can further be reacted with the Grignard reagent of the formula (XXII) in the same manner as in the processes of the first and second aspects of this invention. By this further latter Grignard reaction, consequently there is formed the tri-organo-monoalkoxysilane of the above formula (XXVa) which is the target product of the fourth aspect process of this invention. Further, in Procedure (A), an amount of the remaining unreacted Grignard reagent of the formula (XXII) still existing in the reaction mixture or system can also react directly with one to two chloro groups of the starting chlorosilane compound (XXI) as added later, and thus there proceeds concurrently some reaction of another route for the production of organo-chlorosilane derivatives which contain one to two groups of the secondary alkyl group, tertiary alkyl group, a cycloalkyl group or an aryl group for R. Some other different side-reactions can also occur concurrently.

(ii) Next, in Procedure (B) of the fourth aspect process of this invention, the reaction of the chloro silane of the formula (XXI) with the Grignard reagent of the formula (XXII) is effected by admixing and reacting at first the Grignard reagent of the formula (XXII) with tetrachlorosilane or a di or mono-organo-di or trichlorosilane of the formula (XXI), then adding to the so obtained reaction mixture containing therein the Grignard reagent and the resulting reaction product of the reaction of the Grignard reagent with tetrachlorosilane or the di or mono-organo-di or trichlorosilane an amount of the alcohol of the formula (XXIII) or the alkylene oxide or glycidylether of the formula (XXIV), and effecting further reactions between the Grignard reagent, said reaction product and the added alcohol or the added alkylene oxide or glycidylether present in the resultant mixture, to produce the tri-organo-mono-(alkoxy, cycloalkyloxy or aralkyloxy) silane of the formula (XXVa).

In this Procedure (B), too, the Grignard reagent of the formula (XXII) is to be used in a proportion of 1-10 moles, preferably 2-5 moles per 1 mole of the chlorosilane compound (XXI) for effecting the reaction. The alcohol (XXIII) or the epoxy compound (XXIV) is to be used in a proportion of 0.5-2 moles, preferably 0.5-1.5 moles per 1 mole of the chlorosilane compound (XXI) for effecting the reaction.

In this Procedure (B), it is possible to take either the route comprising adding the chlorosilane compound (XXI) to the Grignard reagent of the formula (XXII) and then effecting the reactions, or the route comprising adding the Grignard reagent of the formula (XXII) to the chlorosilane compound (XXI) and then effecting the reactions. In both the routes, in the resulting reaction mixture or solution, there has been formed a chlorosilane derivative which has been produced as the intermediate reaction product by the direct reaction of the Grignard reagent of the formula (XXII) with the chlorosilane compound (XXI). When the alcohol (XXIII) or the epoxy compound (XXIV) is then later added to the said resulting reaction mixture or solution as above, said alcohol or epoxy compound as added can presumably be reacted with an amount of the remaining unreacted Grignard reagent of the formula (XXII). It is further presumable that the later occurring reaction will produce the alkoxy-magnesium halide of the formula (XXVIa) or (XXVIb) similarly to that in the Procedure (A) above, and that the alkoxy-magnesium halide thus produced can further be reacted with the chlorosilane compound (XXI), thereby to produce the aforesaid intermediate chlorosilane derivative (XXVIIa) or (XXVIIb). Thus, consequently the tri-organo-monoalkoxysilane of the formula (XXVa), which is the target product of the fourth aspect process of this invention, is produced through various routes by the Grignard reaction.

In the fourth aspect process of this invention, by either one of Procedure (A) and Procedure (B), the reactions in the process may be carried out in an ether solvent or in a mixed solvent of an ether solvent with an aprotic organic solvent. As the ether solvent, there may be mentioned, for example, diethylether, tetrahydrofuran, and the like. As the aprotic organic solvent, there may be used a hydrocarbon solvent such as hexane, heptane, toluene, xylene and the like.

The reactions may be conducted at a temperature in the range of 0-150° C., preferably 30-150° C. Further, it is preferable to carry out the reactions under an inert gas atmosphere such as nitrogen, argon and the like, because the presence of oxygen in the reaction system brings about undesirable reaction of oxygen with the Grignard reagent, resulting in lowering of the yield of the desired target product.

In the fourth aspect process of this invention, the reactions with the Grignard reagent is conducted as usual for 1-24 hours until a completion of the reaction. Subsequently, a suitable amount of a saturated aqueous ammonium chloride solution or dilute sulfuric acid is mixed with the final reaction mixture or solution as obtained after the completion of the reaction, so that the deposited inorganic magnesium salt can be dissolved in the aqueous ammonium chloride solution or in the dilute sulfuric acid. The organic layer in the reaction solution is then separated from the resulting aqueous layer, and the organic layer as separated is subjected to a fractional distillation (that is, rectification) under an atmospheric or reduced pressure, and thus there can be isolated and recovered the desired tri-organo-mono(2-substituted or unsubstituted alkoxy or cycloalkyloxy or aralkyloxy)silane of the formula (XXVa).

By the way, when the reaction is effected with using such Grignard reagent of the formula (XXII) which contains a highly bulky tertiary alkyl group such as tert-butyl group, there is a possibility that the desired tri-tert-alkyl-substituted-mono(alkoxy, cycloalkyloxy or aralkyloxy)-silane would be produced only in a very low yield, even if the reaction has been effected for a long period of time.

The tri-organo-mono(alkoxy, cycloalkyloxy or aralkyloxy)silane of the formula (XXVa) may alternatively be represented by the formula (XVa-1)

wherein $R^1$, $R^2$, R, x and y each have the same meanings as defined in the formulae (XXI), (XXII) and (XXIII) above, and $R^7$ has the same meaning as $R^3$ of the formula (XXIII) above, or $R^7$ is the group of the formula $—CH_2—CH(R)—R^4$ where R and $R^4$ have the same meanings as defined above.

Concrete examples of the tri-organo-mono(alkoxy, cycloalkyloxy or aralkyloxy)silane derivative of the formula (XXVa) as produced by the fourth aspect process of this invention may include triisopropylmethoxysilane, triisopropylethoxysilane, triisopropylisopropoxysilane, triisopropyl-n-butoxysilane, triisopropyl-3-methylbutoxysilane, triisopropylbenzyloxysilane, tri-sec-butylmethoxysilane, tri-sec-butylethoxysilane, tri-sec-butylisopropoxysilane, tri-sec-butyl-n-butoxysilane, tri-sec-butyl-3-methylpentyloxysilane, tri-sec-butylbenzyloxysilane; and tricyclohexylmethoxysilane, tricyclohexylethoxysilane, tricyclohexylisopropoxysilane, tricyclohexyl-n-butoxysilane, tricyclohexyl-2-cyclohexylethoxysilane, tricyclohexylbenzyloxysilane; and tri-o-tolylmethoxysilane, tri-o-tolylethoxysilane, tri-o-tolylisopropoxysilane, tri-o-tolyl-n-butoxysilane, tri-o-tolyl-2-o-tolylethoxysilane, tri-o-tolylbenzyloxysilane; diisopropylmethylmethoxysilane, diisopropylmethylethoxysilane, diisopropylmethylisopropoxysilane, diisopropylmethyl-n-butoxysilane, diisopropylmethyl-3-methylbutoxysilane, diisopropylmethylbenzyloxysilane, diisopropylvinylmethoxysilane, diisopropylvinylethoxysilane, diisopropylvinylisopropoxysilane, diisopropylvinyl-n-butoxysilane, diisopropylvinyl-3-methylbutoxysilane, diisopropylvinylbenzyloxysilane, diisopropylphenylmethoxysilane, diisopropylphenylethoxysilane, diisopropylphenylisopropoxysilane, diisopropylphenyl-n-butoxysilane, diisopropylphenyl-3-methylbutoxysilane, diisopropylphenylbenzyloxysilane, di-sec-butylmethylmethoxysilane, di-sec-butylmethylethoxysilane, di-sec-butylmethylisopropoxysilane, di-sec-butylmethyl-n-butoxysilane, di-sec-butylmethyl-3-methylpentyloxysilane, di-sec-butylmethylbenzyloxysilane, di-sec-butylvinylmethoxysilane, di-sec-butylvinylethoxysilane, di-sec-butylvinylisopropoxysilane, di-sec-butylvinyl-n-butoxysilane, di-sec-butylvinyl-3-methylpentyloxysilane, di-sec-butylvinylbenzyloxysilane, di-sec-butylphenylmethoxysilane, di-sec-butylphenylethoxysilane, di-sec-butylphenylisopropoxysilane, di-sec-butylphenyl-n-butoxysilane, di-sec-butylphenyl-3-methylpentyloxysilane, di-sec-butylphenylbenzyloxysilane, dicyclohexylmethylmethoxysilane, dicyclohexylmethylethoxysilane, dicyclohexylmethylisopropoxysilane, dicyclohexylmethyl-n-butoxysilane, dicyclohexylmethyl-2-cyclohexylethoxysilane, dicyclohexylmethylbenzyloxysilane, dicyclohexylvinylmethoxysilane, dicyclohexylvinylethoxysilane, dicyclohexylvinylisopropoxysilane, dicyclohexylvinyl-n-butoxysilane, dicyclohexylvinyl-2-cyclohexylethoxysilane, dicyclohexylvinylbenzyloxysilane, dicyclohexylphenylmethoxysilane, dicyclohexylphenylethoxyilane, dicyclohexylphenylisopropoxysilane, dicyclohexylphenyl-n-butoxysilane, dicyclohexylphenyl-2-cyclohexylethoxysilane, dicyclohexylphenylbenzyloxysilane, di-o-tolylmethylmethoxysilane, di-o-tolylmethylethoxysilane, di-o-tolylmethylisopropoxysilane, di-o-tolylmethyl-n-butoxysilane, di-o-tolylmethyl-2-o-tolylethoxysilane, di-o-tolylmethylbenzyloxysilane, di-o-tolylvinylmethoxysilane, di-o-tolylvinylethoxysilane, di-o-tolylvinylisopropoxysilane, di-o-tolylvinyl-n-butoxysilane, di-o-tolylvinyl-2-o-tolylethoxysilane, di-o-tolylvinylbenzyloxysilane, di-o-tolylphenylmethoxysilane, di-o-tolylphenylethoxysilane, di-o-tolylphenylisopropoxysilane, di-o-tolylphenyl-n-butoxysilane, di-o-tolylphenyl-2-o-tolylethoxysilane, di-o-tolylphenylbenzyloxysilane, isopropyldiphenylmethoxysilane, isopropyldiphenylethoxysilane, isopropyldiphenylisopropoxysilane, isopropyldiphenyl-n-butoxysilane, isopropyldiphenyl-3-methylbutoxysilane, isopropyldiphenylbenzyloxysilane, sec-butyldiphenylmethoxysilane, sec-butyldiphenylethoxysilane, sec-butyldiphenylisopropoxysilane, sec-butyldiphenyl-n-butoxysilane, sec-butyldiphenyl-3-methylpentyloxysilane, sec-butyldiphenylbenzyloxysilane, cyclohexyldiphenylmethoxysilane, cyclohexyldiphenylethoxysilane, cyclohexyldiphenylisopropoxysilane, cyclohexyldiphenyl-n-butoxysilane, cyclohexyldiphenyl-2-cyclohexylethoxysilane, cyclohexyldiphenylbenzyloxysilane, o-tolyldiphenylmethoxysilane, o-tolyldiphenylethoxysilane, o-tolyldiphenylisopropoxysilane, o-tolyldiphenyl-n-butoxysilane, o-tolyldiphenyl-2-o-tolylethoxysilane, o-tolyldiphenylbenzyloxysilane, tert-butyldiphenylmethoxysilane, tert-butyldiphenylethoxysilane, tert-butyldiphenylisopropoxysilane, tert-butyldiphenyl-n-butoxysilane, tert-butyldiphenyl-3,3-dimethylbutoxysilane, tert-butyldiphenylbenzyloxysilane, tert-butylphenylmethylmethoxysilane, tert-butylphenylmethylethoxysilane, tert-butylphenylmethylisopropoxysilane, tert-butylphenylmethyl-n-butoxysilane, tert-butylphenylmethyl-3,3-dimethylbutoxysilane, and the like, but this particular examples do not limit the scope of the object silane product of the formula (XXVa) in any way.

Of the silane product which can be produced by the fourth aspect process of this invention, triisopropylmonoalkoxysilane, tri-sec-butyl-monoalkoxysilane, tricyclohexylmonoalkoxysilane and tert-butyldimethylmonoalkoxysilane are particularly useful as a starting material for the synthesis of tri-organo-chlorosilanes which are to be used as the sylilating agent for protecting a functional hydroxyl group of various synthetic intermediates that are produced in the preparation of medicines and the like. They are also useful in other applications.

According to the production process of the fourth aspect of this invention which needs only the facile operations for the reaction, there can be produced a tri-organo-mono-alkoxy or cycloalkyloxy or aralkyloxysilane compound containing the bulky hydrocarbon group or groups and having the general formula (XXVa) in a high yield without any necessity of using the lithium catalyst difficult to handle, and without any necessity of using any highly toxic catalyst.

BEST MODE FOR CARRYING OUT THE INVENTION

Now, the processes according to the first and second aspects of this invention are illustrated by Examples 1-10 and Example 43.

EXAMPLE 1

(a) Preparation of a Monoalkoxy-Trichlorosilane as the Starting Compound

A four-necked flask (200 ml-capacity) fitted with a stirrer, a thermometer and a Dimroth was charged with 102 g (0.6 moles) of tetrachlorosilane (namely, silicon tetrachloride). To the flask was then added dropwise 44 g (0.6 moles) of n-butanol over 1 hour at a temperature of 10° C.-25° C. in the flask. The resulting reaction mixture was then heated under stirring at a temperature of 60° C.-70° C. for 1 hour. There was obtained a reaction solution containing n-butoxytrichlorosilane as produced. This reaction solution was subjected to a rectification (a fractional distillation) under a reduced pressure. Thus, there was afforded 50 g of n-butoxytrichlorosilane (one example of the compounds of the general formula (I)) as a fraction boiling at 66° C.-74° C./62 mm Hg.

Analysis of this product by a gas chromatography showed the purity of 98%.

(b) Preparation of a Grignard Reagent

A four-necked flask (one-liter-capacity) fitted with a stirrer, a thermometer and a Dimroth was charged with 16.0 g (0.66 moles) of metallic magnesium, 270 ml of an organic solvent, tetrahydrofuran, and a small amount of iodine. To the resulting mixture was added dropwise 51.8 g (0.66 moles) of isopropyl chloride under a nitrogen gas atmosphere at a temperature of 40° C.-50° C. in the flask over 1 hour. The resulting reaction mixture was then heated under stirring at 50° C. for 1 hour, thus affording a reaction solution containing isopropyl magnesium chloride (the Grignard reagent) as produced.

(c) Grignard Reaction

To the solution in tetrahydrofuran (THF) of isopropyl magnesium chloride (the Grignard reagent) as obtained in (b) above was added dropwise 41.5 g (0.2 moles) of the n-butoxytrichlorosilane produced in (a) above, at 30° C.-40° C. over 1 hour. To the resulting reaction mixture was then added 150 ml of toluene, and the mixture so obtained was stirred at a temperature of 90° C. in the flask for 4 hours to conduct the Grignard reaction. To the resulting Grignard reaction solution was added dropwise 120 ml of a saturated aqueous ammonium chloride solution to dissolve the precipitated magnesium salt ($MgCl_2$). The resulting mixture was then separated into an aqueous layer and an organic layer. The organic layer was subjected to a distillation, and thus, 42 g of triisopropyl-n-butoxysilane was isolated as a fraction boiling at 96° C.-103° C./12 mm Hg (yield; 90%).

EXAMPLE 2

A Grignard reagent was prepared in accordance with the procedure of Example 1(b), except that 61.1 g (0.66 moles) of sec-butyl chloride was used instead of isopropyl chloride. The sec-butyl magnesium chloride thus obtained was reacted with 105 g (0.2 moles) of n-butoxytrichlorosilane in the same manner as in Example 1(b) for the intended Grignard reaction. Thus, 49 g of tri-sec-butyl-n-butoxysilane was obtained as a fraction boiling at 106° C.-108° C./3 mm Hg (yield; 88%).

EXAMPLE 3

(a) Preparation of Grignard Reagent

A four-necked flask (500 ml-capacity) fitted with a stirrer, a thermometer and a Dimroth was charged with 16.0 g (0.66 moles) of metallic magnesium, 270 ml of tetrahydrofuran (THF) as an organic solvent and a small amount of iodine. To the resulting mixture was added dropwise 51.8 g (0.66 moles) of isopropyl chloride under a nitrogen gas atmosphere over 1 hour. During the dropwise addition, the reaction mixture in the flask was maintained at a temperature of 40° C.-50° C. Then, the reaction mixture was heated under stirring at 50° C. for 1 hour, to obtain a THF solution of isopropyl magnesium chloride.

(b) Preparation of a Monoalkoxy-Trichlorosilane as the Starting Compound

A one liter-capacity, four-necked flask fitted with a stirrer, a thermometer and a Dimroth was charged with 34.0 g (0.2 moles) of tetrachlorosilane, to which was then added dropwise 6.4 g (0.2 moles) of methanol over 1 hour. During the dropwise addition, the mixture in the flask was maintained at 10° C.-25° C. Then, the reaction mixture in the flask was heated under stirring at 50° C. for 1 hour. Thus, there was obtained a reaction solution containing methoxytrichlorosilane as produced.

(c) Grignard Reaction

The THF solution of isopropyl magnesium chloride (Grignard reagent) as prepared in (a) above was added dropwise through a dropping funnel to a solution containing methoxytrichlorosilane, that is, the reaction solution as obtained in (b) above, at 30° C.-40° C. over 1 hour. Then, to the resulting mixture was added 150 ml of toluene, and the mixture was stirred at a temperature of 90° C. in the flask for 4 hours to conduct the Grignard reaction. Then, 120 ml of a saturated aqueous ammonium chloride solution was added dropwise to the resulting Grignard reaction solution to dissolve the magnesium salt. The organic layer was separated from the aqueous layer and then subjected to a fractional distillation under a reduced pressure, thus yielding 27 g of triisopropylmethoxysilane as a fraction boiling at 85° C.-86° C./20 mm Hg (yield; 70%).

EXAMPLE 4

8.8 g (0.2 moles) of ethylene oxide was used in place of methanol as used in Example 3(b) and was reacted with 34.0 g of tetrachlorosilane in the same manner as in Example 3(b). Thus, there was obtained a reaction solution containing 2-chloroethoxytrichlorosilane. Then, a Grignard reaction was effected by adding the THF solution of isopropyl magnesium chloride to the 2-chloroethoxytrichlorosilane in the same manner as in Example 3(c). The post-treatment of the Grignard reaction solution so obtained was carried out in the same manner as in Example 3(c), and the separated organic layer was distilled to afford 48 g of triisopropyl-2-chloroethoxysilane as a fraction boiling at 118° C.-120° C./5 mm Hg (yield; 71%).

EXAMPLE 5

61.1 g (0.66 moles) of sec-butyl chloride was used in place of isopropyl chloride as used in Example 3(a), and the reaction of it with 16.0 g of metallic magnesium in THF was conducted in the same manner as in Example 3(a). Thus, there was obtained a THF solution of sec-butyl magnesium chloride. This THF solution of the Grignard reagent was added dropwise to the methoxytrichlorosilane solution as prepared in Example 3(b), in the same manner as in Example 3(c) to effect the Grignard reaction.

The resulting Grignard reaction solution was post-treated with a saturated aqueous ammonium chloride solution in the same manner as in Example 3(c). The organic layer was separated from the aqueous layer and was fractionally distilled under a reduced pressure to afford 32 g of tri-sec-butylmethoxysilane as a fraction boiling 88° C.-91° C./5 mm Hg (yield; 68%).

EXAMPLE 6

78.3 g (0.66 moles) of cyclohexyl chloride was used in place of isopropyl chloride as used in Example 3(a) and was reacted with 16.0 g of metallic magnesium in THF in the same manner as in Example 3(a). There was thus obtained a THF solution of cyclohexyl magnesium chloride.

On the other hand, 14.8 g (0.2 moles) of n-butanol was used in place of methanol as used in Example 3(b) and was reacted with 34.0 g of tetrachlorosilane in the same manner as in Example 3(b). There was thus obtained a solution of n-butoxytrichlorosilane.

The THF solution of cyclohexyl magnesium chloride (Grignard reagent) as prepared above was added dropwise to the n-butoxytrichlorosilane solution as prepared above, in the same manner as in Example 3(c), followed by effecting the Grignard reaction.

The resulting Grignard reaction solution was post-treated with a saturated aqueous ammonium chloride solution in the same manner as in Example 3(c). The organic layer was separated from the aqueous layer. The solvent was distilled off under a reduced pressure from the organic layer, to afford crude crystals of tricyclohexyl-n-butoxysilane. Recrystallization from hexane gave 47 g of tricyclohexyl-n-butoxysilane (yield; 65%).

EXAMPLE 7

The reaction of Example 3(a) was repeated except that the metallic magnesium was used in an amount of 10.7 g (0.44 moles) instead of 16.0 g (0.66 moles), the THF was used in an amount of 180 ml instead of 270 ml and the isopropyl chloride was used in an amount of 34.6 g (0.44 moles) instead of 51.8 g (0.66 moles). Thereby, there was obtained a THF solution of isopropyl magnesium chloride.

On the other hand, 29.9 g (0.2 moles) of methyltrichlorosilane was used in place of tetrachlorosilane as used in Example 3(b) and was reacted with methanol in the same manner as in Example 3(b). There was thus obtained a THF solution of methylmethoxydichlorosilane.

The THF solution of isopropyl magnesium chloride as obtained above was added dropwise to the solution of methylmethoxydichlorosilane as obtained above, in the same manner as in Example 3(c), to effect the Grignard reaction. The resulting Grignard reaction solution was post-treated similarly as in Example 3(c) with a saturated aqueous ammonium chloride solution in a reduced amount of 80 ml instead of the 120 ml as used in Example 3(c). The organic layer was separated and was subjected to a fractional distillation under a reduced pressure, thereby to afford 26 g of diisopropylmethylmethoxysilane as a fraction boiling at 55° C.-56° C./43 mmHg (yield; 78%).

EXAMPLE 8

The metallic magnesium used in Example 5 was used in a reduced amount of 10.7 g (0.44 moles) instead of 16.0 g (0.66 moles), and the THF was used in a reduced amount of 180 ml instead of 270 ml, and the sec-butyl chloride was used in a reduced amount of 40.8 g (0.44 moles). These reaction components were reacted in the same manner as in Example 3(a), thereby to obtain a THF solution of sec-butyl magnesium chloride.

The sec-butyl magnesium chloride as prepared above was added dropwise to the methylmethoxydichlorosilane solution as obtained in Example 7, in the same manner as in Example 3(c), to effect the Grignard reaction. The resulting Grignard reaction solution was post-treated with the saturated aqueous ammonium chloride solution as used in Example 3(c) in a reduced amount of 80 ml, instead of the 120 ml. The organic layer was separated and was subjected to a fractional distillation, thereby to afford 31 g of di-sec-butyl methylmethoxysilane as a fraction boiling at 76° C.-78° C./16 mmHg (yield; 80%).

EXAMPLE 9

The metallic magnesium as used in Example 6 was used in a reduced amount of 10.7 g (0.44 moles) instead of 16.0 g (0.66 moles), and the THF was used in a reduced amount of 180 ml instead of 270 ml, and the cyclohexyl chloride was used in a reduced amount of 52.2 g (0.44 moles) instead of 78.3 g (0.66 moles). The reaction components were reacted in the same manner as in Example 6, thereby to obtain a THF solution of cyclohexyl magnesium chloride.

The THF solution of cyclohexyl magnesium chloride as prepared above was added dropwise to the methylmethoxydichlorosilane solution obtained in Example 7, in the same manner as in Example 3(c), to effect the Grignard reaction. The post-treatment of the resulting Grignard reaction solution was carried out in the same manner as in Example 3(c), except that the saturated aqueous ammonium chloride solution used in Example 3(c), was used in a reduced amount of 80 ml instead of 120 ml. The organic layer was separated and was fractionally distilled under a reduced pressure, thereby to afford 39 g of dicyclohexylmethylmethoxysilane as a fraction boiling at 128° C.-129° C./7 mm Hg (yield; 80%).

EXAMPLE 10

(a) Preparation of a Grignard Reagent

A 200 ml-capacity, four-necked flask fitted with a stirrer, a thermometer and a Dimroth was charged with 5.3 g (0.22 moles) of metallic magnesium, 90 ml of tetrahydrofuran (THF) and a small amount of iodine. To the resulting mixture was added dropwise 17.3 g (0.22 moles) of isopropyl chloride under a nitrogen gas atmosphere at 40° C.-50° C. over 1 hour. Then, the resulting reaction mixture was heated under stirring at 50° C. for 1 hour, thereby to obtain a THF solution of isopropyl magnesium chloride (Grignard reagent).

(b) Preparation of an Organo-Substituted-Mono Alkoxy-Chlorosilane by Disproportionation Reaction A 500 ml-capacity, four-necked flask was charged with 18.5 g (0.1 moles) of diisopropyldichlorosilane and 17.6 g (0.1 moles) of diisopropyldimethoxysilane, and the resulting mixture was stirred at 20° C.-30° C. for 1 hour. There occurred a disproportionation reaction, thus giving a mixture comprising diisopropylmethoxychlorosilane, the unreacted diisopropyldichlorosilane and the unreacted diisopropyldimethoxysilane.

(c) Grignard Reaction

To the mixture of the silanes containing diisopropylmethoxychlorosilane as obtained from the disproportionation reaction in (b) above, was added 150 ml of toluene to dissolve the mixture, thereby to obtain a toluene solution of the said silane mixture. The THF solution of isopropyl magnesium chloride (Grignard reagent) as prepared in (a) above was added dropwise through a dropping funnel to the toluene solution of said silane mixture at 40° C.-50° C. over 1 hour. Then the resulting mixture was stirred at 70° C. for 4 hours.

Thus, the Grignard reagent was reacted with the diisopropylmethoxychlorosilane contained in the said toluene solution, to produce triisopropylmethoxysilane. To the resulting reaction solution was added dropwise 40 ml of a saturated aqueous ammonium chloride solution to dissolve the magnesium salt in the latter. The organic layer was separated from the aqueous layer and the organic layer, was distilled to afford 28 g of triisopropylmethoxysilane as a fraction boiling at 85° C.-86° C./20 mm Hg. The yield was 73%.

The following Examples 11-31 illustrate the preparation of tri-organo-monochlorosilanes by the process according to the third aspect of this invention.

EXAMPLE 11

A 500 ml-capacity, four-necked flask fitted with a stirrer, a thermometer and a Dimroth was charged with 29.3 g (0.2 moles) of triethylmethoxysilane. To the flask was then added 400 g of 35% hydrochloric acid. The resulting mixture was stirred at 20° C. for 10 hours to conduct the reaction. The resulting reaction solution was separated into the aqueous layer and the organic layer. The organic layer was distilled to afford 28 g of triethylchlorosilane as a fraction boiling at 142° C.-144° C. (yield; 900).

EXAMPLE 12

A 500 ml-capacity, four-necked flask fitted with a stirrer, a thermometer and a Dimroth was charged with 29.3 g (0.2 moles) of tert-butyldimethylmethoxysilane. To the flask was then added 400 g of 35% hydrochloric acid, and the resulting mixture was stirred at 20° C. for 5 hours to effect the reaction. There were deposited crystals, which crystals were then filtered off. The crystals obtained were subjected to a distillation at atmospheric pressure to afford 29 g of tert-butyldimethylchlorosilane as a fraction boiling at 125° C. (yield; 95%).

EXAMPLE 13

A 500 ml-capacity, four-necked flask fitted with a stirrer, a thermometer and a Dimroth was charged with 37.7 g (0.2 moles) of triisopropylmethoxysilane. To the flask was then added 150 g of 35% hydrochloric acid, and the resulting mixture was stirred at 20° C. for 10 hours to effect the reaction. The resulting reaction solution was separated into the aqueous layer and the organic layer. The organic layer was distilled to afford 38 g of triisopropylchlorosilane as a fraction boiling at 78° C.-80° C./10 mm Hg (yield; 99%).

EXAMPLE 14

The procedure of Example 13 was repeated except that triisopropylmethoxysilane was replaced by 83.3 g (0.2 moles) of triisopropyl-n-butoxysilane. The latter was reacted with 35% hydrochloric acid. There was obtained 38 g of triisopropylchlorosilane (yield; 99%).

EXAMPLE 15

(a) Preparation of a Monoalkoxytrichlorosilane

A 200 ml-capacity, four-necked flask fitted with a stirrer, a thermometer and a Dimroth was charged with 102 g (0.6 moles) of tetrachlorosilane (silicon tetrachloride). To the latter was then added dropwise 44 g (0.6 moles) of n-butanol at a temperature of the resultant mixture of 10° C.-25° C. over 1 hour. The resulting reaction mixture was then heated under stirring at 60° C.-7° C. for 1 hour. There was obtained a reaction solution containing n-butoxy-trichlorosilane so produced. The reaction solution was subjected to a rectification (a fractional distillation). There was thus afforded 50 g of n-butoxytrichlorosilane as a fraction boiling at 66° C.-74° C./62 mm Hg. This product showed a purity of 98% when analized by a gas chromatography.

(b) Preparation of Grignard Reagent

A one liter-capacity, four-necked flask fitted with a stirrer, a thermometer and a Dimroth was charged with 16.0 g (0.66 moles) of metallic magnesium, 270 ml of an organic solvent, tetrahydrofuran, and a small amount of iodine. To the resulting mixture was added dropwise 51.8 g (0.66 moles) of isopropyl chloride under a nitrogen gas atmosphere at 40° C.-50° C. over 1 hour. The resulting reaction mixture was then heated at 50° C. under stirring for 1 hour, thereby to obtain a reaction solution containing isopropyl magnesium chloride (Grignard reagent) so produced.

(c) Grignard Reaction

To the resulting tetrahydrofuran (THF) solution of isopropyl magnesium chloride (Grignard reagent) so obtained in (b) above was added dropwise 41.5 g (0.2 moles) of n-butoxytrichlorosilane as obtained in (a) above, at 30° C.-40° C. over 1 hour. Subsequently, 150 ml of toluene was added to the resulting reaction mixture, and the mixture so obtained was stirred at a temperature of the mixture of 90° C. for 4 hours to conduct the Grignard reaction.

To the resultant reaction solution was added dropwise 120 ml of a saturated aqueous ammonium chloride solution to dissolve the magnesium salt ($MgCl_2$) in the latter. The aqueous layer of the resulting mixture was separated from the organic layer, affording the organic layer containing triisopropyl-n-butoxysilane.

(d) Synthesis of a Tri-Organo-Chlorosilane (by the Third Aspect Process of this Invention)

To the reaction solution containing triisopropyl-n-butoxysilane as obtained in (c) above was added 150 g of 35% hydrochloric acid. The resultant mixture was stirred at 20° C. for 10 hours to effect the reaction. The resulting reaction solution was separated into the aqueous layer and the organic layer. The organic layer was distilled to afford 35 g of triisopropylchlorosilane as a fraction boiling at 78° C.-80° C./10 mm Hg (yield; 89%).

EXAMPLE 16

The preparation of a Grignard reagent in accordance with the procedure of Example 15(b) was repeated except that isopropyl chloride was replaced by 61.1 g (0.66 moles) of sec-butyl chloride. The sec-butyl magnesium chloride so produced was reacted with 41.5 g (0.2 moles) of n-butoxytrichlorosilane in the same manner as in Example 15(c) for the Grignard reaction. The resulting reaction solution containing tri-sec-butyl-n-butoxysilane so produced was post-treated in the same manner as in Example 15(c) to obtain the organic layer containing tri-sec-butyl-n-butoxysilane.

The resulting organic layer was treated with 35% hydrochloric acid in the same manner as in Example 15(d). The organic layer was separated from the aqueous layer and was subjected to a fractional distillation under a reduced pressure to afford 41 g of tri-sec-butylchlorosilane as a fraction boiling at 93° C.-95° C./5 mm Hg (yield; 86%).

EXAMPLE 17

(a) Preparation of Grignard Reagent

A 500 ml-capacity, four-necked flask fitted with a stirrer, a thermometer and a Dimroth was charged with 16.0 g (0.66 moles) of metallic magnesium, 270 ml of an organic solvent, tetrahydrofuran (THF) and a small amount of iodine. To the resulting mixture was added dropwise 51.8 g (0.66 moles) of isopropyl chloride under a nitrogen gas atmosphere over 1 hour. During the dropwise addition, the temperature of the reaction mixture in the flask was kept at 40° C.-50° C. Then, the reaction mixture was heated at 50° C. under stirring for 1 hour, thereby to obtain a THF solution of isopropyl magnesium chloride.

(b) Preparation of a Monoalkoxy-Trichlorosilane to be Used as Starting Compound

A one liter-capacity, four-necked flask fitted with a stirrer, a thermometer and a Dimroth was charged with 34.0 g (0.2 moles) of tetrachlorosilane. There was then added dropwise 6.4 g (0.2 moles) of methanol over 1 hour. During the dropwise addition, the temperature of the reaction mixture in the flask was kept at 10° C.-25° C. Then, the reaction mixture in the flask was heated at 50° C. under stirring for 1 hour. There was obtained a reaction solution containing methoxytrichlorosilane so produced.

(c) Grignard Reaction

To the solution containing methoxytrichlorosilane, which is the reaction solution obtained in (b) above, was added the THF solution of isopropyl magnesium chloride (Grignard reagent) as prepared in (a) above, through a dropping funnel at 30° C.-40° C. over 1 hour. To the resulting mixture was then added 150 ml of toluene, and the mixture so obtained was stirred at a temperature of the mixture of 90° C. for 4 hours to effect the Grignard reaction.

To the resulting reaction solution was added dropwise 120 ml of a saturated aqueous ammonium chloride solution to dissolve the magnesium salt. The resulting mixture was separated into the aqueous layer and the organic layer, thus to afford the organic layer containing triisopropylmethoxysilane.

(d) Synthesis of a Tri-Organo-Chlorosilane (by the Third Aspect Process of this Invention)

The triisopropylmethoxysilane in the organic layer as obtained in (c) above was reacted with 35% hydrochloric acid in the same manner as in Example 15(d). The organic layer was separated from the aqueous layer and was subjected to a fractional distillation under a reduced pressure. There was thus obtained 27 g of triisopropylchlorosilane as a fraction boiling at 78° C.-80° C./10 mm Hg (yield; 69%).

EXAMPLE 18

The procedure of Example 17(b) was repeated except that methanol used in Example 17(b) was replaced by 8.8 g (0.2 moles) of ethylene oxide. Then, 34.0 g of tetrachlorosilane was reacted with ethylene oxide. Thus, there was obtained a reaction solution containing 2-chloroethoxytrichlorosilane. Subsequently, a THF solution of isopropyl magnesium chloride was added to said reaction solution and the Grignard reaction was effected as in Example 17(c). The resulting reaction solution was post-treated in the same manner as in Example 17(c), thereby to obtain the organic layer containing triisopropyl-2-chloroethoxysilane.

The resulting organic layer was treated with 35% hydrochloric acid in the same manner as in Example 15(d). The organic layer was separated from the aqueous layer and was subjected to a fractional distillation under a reduced pressure. There was thus afforded 28 g of triisopropylchlorosilane as a fraction boiling at 78° C.-80° C./10 mm Hg (yield; 70%).

EXAMPLE 19

The procedure of Example 17(a) was repeated except that isopropyl chloride used in Example 17(a) was replaced by 78.3 g (0.66 moles) of cyclohexyl chloride. Thus, a THF solution of cyclohexyl magnesium chloride was obtained.

The THF solution of the so produced Grignard reagent was added dropwise to the solution of methoxytrichlorosilane as prepared in Example 17(b), followed by effecting the Grignard reaction in the same manner as in Example 17(c). The resulting Grignard reaction solution was post-treated with a saturated aqueous ammonium chloride solution in the same manner as in Example 17(c), and then there was separated the organic layer containing tricyclohexylmethoxysilane.

The resulting organic layer was treated with 35% hydrochloric acid in the same manner as in Example 15(d). The organic layer was separated from the aqueous layer and was concentrated under a reduced pressure, to give crystals. The resulting crystals were recrystallized from hexane to give 41 g of tricyclohexylchlorosilane (yield; 64%).

EXAMPLE 20

The procedure of Example 17(a) was repeated except that isopropyl chloride used in Example 17(a) was replaced by 20.4 g (0.22 moles) of tert-butyl chloride. The latter was reacted with 5.3 g (0.22 moles) of metallic magnesium in 90 ml of THF. There was thus obtained a THF solution of tert-butyl magnesium chloride.

On the other hand, the procedure of Example 17(b) was repeated except that tetrachlorosilane used in Example 17(b) was replaced by 25.8 g (0.2 moles) of dimethyldichlorosilane. The latter was reacted with methanol in the same manner as in Example 17(b). Thus, there was obtained a solution of dimethylmethoxychlorosilane.

The THF solution of tert-butyl magnesium chloride obtained as above was added dropwise to the solution of dimethylmethoxychlorosilane obtained as above, followed by effecting the Grignard reaction in the same manner as in Example 17(c). The resulting reaction solution was post-treated with a saturated aqueous ammonium chloride solution in the way same as that in Example 17(c), while the aqueous NH$_4$Cl solution was used in a reduced amount of 40 ml, but not 120 ml. There was obtained an organic layer containing tert-butyldimethylmethoxysilane.

The resulting organic layer was treated with 35% hydrochloric acid in the same manner as in Example 15(d), while an increased amount of the hydrochloric acid of 300 ml was used. The organic layer was separated from the aqueous layer and was subjected to a fractional distillation at atmospheric pressure, thus to afford 15 g of tert-butyldimethylchlorosilane as a fraction boiling at 124° C.-125° C. (yield; 60%).

EXAMPLE 21

(a) Preparation of an Organo-Substituted-Monoalkoxysilane by Disproportionation Reaction A 500 ml-capacity, four-necked flask was charged with 12.9 g (0.1 moles) of dimethyldichlorosilane and 12.0 g (0.1 moles) of dimethyldimethoxysilane, and the resulting mixture was stirred at 20° C.-30° C. for 1 hour. Thus, there occurred a disproportionation reaction to produce dimethylmethoxychlorosilane, so that there was obtained a silane mixture comprising the dimethylmethoxychlorosilane, the unreacted dimethyldichlorosilane and the unreacted dimethyldimethoxysilane.
(b) Grignard Reaction To the silane mixture comprising dimethylmethoxychlorosilane as produced by the disproportionation reaction in (a) above, was added 150 ml of toluene to dissolve the silanes in toluene, and to give a toluene solution of said silane mixture.

To the toluene solution was added dropwise the THF solution of tert-butyl magnesium chloride as produced in Example 20, through a dropping funnel, at 40° C.-50° C. over 1 hour. Then, the resulting mixture was stirred at 70° C. for 4 hours. The Grignard reagent could react with dimethylmethoxychlorosilane contained in the said toluene solution, to produce tert-butyldimethylmethoxysilane.

To the resulting reaction solution was added dropwise 40 ml of a saturated aqueous ammonium chloride solution to dissolve the magnesium salt. The aqueous layer of the resulting mixture was separated from the organic layer, thereby to obtain the organic layer containing tert-butyldimethylmethoxysilane.
(c) Synthesis of a Tri-Organo-Chlorosilane (by the Third Aspect Process of this Invention)

To the reaction solution containing tert-butyldimethylmethoxysilane as obtained in (b) above was added 300 g of 35% hydrochloric acid. The resulting mixture was stirred at 20° C. for 10 hours. The resulting reaction mixture was separated into the aqueous layer and the organic layer. The organic layer was subjected to a fractional distillation at atmospheric pressure to afford 15 g of tert-butyldimethylchlorosilane as a fraction boiling at 124° C.-125° C. (yield; 60%).

EXAMPLE 22

(a) Preparation of Grignard Reagent

A one liter-capacity, four-necked flask fitted with a stirrer, a thermometer and a Dimroth was charged with 21.4 g (0.88 moles) of metallic magnesium, 360 ml of an organic solvent, tetrahydrofuran, and a small amount of iodide. To the resulting mixture was added dropwise 69.1 g (0.88 moles) of isopropyl chloride under a nitrogen gas atmosphere at a temperature of the mixture of 40° C.-50° C. over 1 hour. The resulting reaction mixture was then heated under stirring at 50° C. for 1 hour, to obtain a reaction solution containing isopropyl magnesium chloride (Grignard reagent) thus produced.
(b) Preparation of a Solution of a Mixture Comprising Magnesium Alkoxides To the THF solution of isopropyl magnesium chloride as obtained in (a) above was added dropwise 6.4 g (0.2 moles) of methanol at a temperature of the mixture of 20° C.-30° C. over 30 minutes. There was thus obtained a solution of a mixture comprising methoxy magnesium chloride as produced and the unreacted isopropyl magnesium chloride.
(c) Grignard Reaction To the above solution of the mixture comprising isopropyl magnesium chloride and methoxy magnesium chloride as obtained in (b) above was added dropwise 34.0 g (0.2 moles) of tetrachlorosilane over 1 hour through a dropping funnel with keeping the resultant mixture at a temperature of 30° C.-40° C. The resulting mixture was stirred at a temperature of the mixture of 75° C. for 4 hours to conduct the Grignard reaction. To the resulting Grignard reaction solution was added dropwise 160 ml of a saturated aqueous ammonium chloride solution to dissolve the magnesium salt. The aqueous layer of the resulting mixture was separated from the organic layer, thus to afford the organic layer containing triisopropylmethoxysilane.
(d) Synthesis of a Tri-Organo-Chlorosilane (by the Third Aspect Process of this Invention)

The organic layer as obtained in (c) above was treated with 35% hydrochloric acid in the same manner as in Example 15(d). The organic layer was separated from the aqueous layer and was subjected to a fractional distillation under a reduced pressure, thus to afford 24 g of triisopropylchlorosilane as a fraction boiling at 78° C.-80° C./10 mm Hg (yield; 60%).

EXAMPLE 23

(a) Grignard Reaction and Alkoxylation Reaction

To the THF solution of isopropyl magnesium chloride as obtained in Example 22(a) was added dropwise 34.0 g (0.2 moles) of tetrachlorosilane through a dropping funnel at a temperature of the resultant mixture of 30° C.-40° C. over 1 hour. To the resultant mixture was then added dropwise 6.4 g (0.2 moles) of methanol through a dropping funnel at a temperature of the mixture of 30° C.-40° C. over 30 minutes. To the resulting mixture was then added 220 ml of toluene, and the resulting mixture was stirred at a temperature of the mixture of 90° C. for 4 hours to complete the Grignard reaction.

To the resulting reaction solution was added dropwise 160 ml of a saturated aqueous ammonium chloride solution to dissolve the magnesium salt. The aqueous layer of the resulting mixture was separated from the organic layer, thus to obtain the organic layer containing triisopropylmethoxysilane.

(b) Synthesis of a Tri-Organo-Chlorosilane (by the Third Aspect Process of this Invention)

The organic layer obtained in (a) above was treated with 35% hydrochloric acid in the same manner as in Example 15(d). The organic layer was separated from the aqueous layer and was subjected to a fractional distillation under a reduced pressure to afford 24 g of triisopropylchlorosilane as a fraction boiling at 78° C.-80° C./10 mm Hg (yield; 60%).

EXAMPLE 24

Instead of methanol used in Example 22(b), 12.0 g (0.2 moles) of isopropanol was used, and isopropanol was reacted with a THF solution of isopropyl magnesium chloride in the same manner as in Example 22(b). There was thus obtained a solution of a mixture comprising isopropoxy magnesium chloride so produced and the unreacted isopropyl magnesium chloride.

The resulting solution of said mixture was reacted with tetrachlorosilane in the same manner as in Example 22(c). The resulting Grignard reaction solution was post-treated in the same manner as in Example 22(c), thus to afford the organic layer containing triisopropylisopropoxysilane.

The organic layer thus obtained was treated with 35% hydrochloric acid in the same manner as in Example 15(d). The organic layer was separated from the aqueous layer and was subjected to a fractional distillation under a reduced pressure to afford 23 g of triisopropylchlorosilane as a fraction boiling at 78° C.-80° C./10 mm Hg (yield; 58%).

EXAMPLE 25

Instead of methanol used in Example 22(b), 8.8 g (0.2 moles) of ethylene oxide was used, and this was reacted with a THF solution of isopropyl magnesium chloride in the same manner as in Example 22(b). There was thus obtained a solution of a mixture comprising 3-methylbutoxy magnesium chloride so produced and the unreacted isopropyl magnesium chloride.

The resulting solution of said mixture was reacted with tetrachlorosilane in the same manner as in Example 22(c). The resulting reaction solution was post-treated in the same manner as in Example 22(c), thus to afford the organic layer containing triisopropyl-3-methylbutoxysilane.

The organic layer thus obtained was reacted with 35% hydrochloric acid in the same manner as in Example 15(d). The organic layer, after it was separated from the aqueous layer, was subjected to a fractional distillation under a reduced pressure to afford 23 g of triisopropylchlorosilane as a fraction boiling at 78° C.-80° C./10 mm Hg (yield; 58%).

EXAMPLE 26

Instead of isopropyl chloride used in Example 22(a), 81.5 g (0.88 moles) of sec-butyl chloride was used, and this was reacted with metallic magnesium in THF in the same manner as in Example 22(a). There was obtained a THF solution of sec-butyl magnesium chloride. The resulting THF solution of sec-butyl magnesium chloride was reacted with methanol in the same manner as in Example 22(b).

Thus, there was obtained a solution of a mixture comprising methoxy magnesium chloride so produced and the unreacted sec-butyl magnesium chloride. To this solution of said mixture was added tetrachlorosilane, and the reaction was made in the same manner as in Example 22(c). The resulting reaction solution was post-treated in the same manner as in Example 22(c), to afford the organic layer containing tri-sec-butylmethoxysilane.

The resulting organic layer was treated with 35% hydrochloric acid in the same manner as in Example 15(d). The organic layer was separated from the aqueous layer and was subjected to a fractional distillation under a reduced pressure, to afford 26 g of tri-sec-butylchlorosilane as a fraction boiling at 93° C.-95° C./5 mm Hg (yield; 54%).

EXAMPLE 27

Instead of isopropyl chloride used in Example 22(a), 104.4 g (0.88 moles) of cyclohexyl chloride was used, and this was reacted with 16.0 g of metallic magnesium in THF in the same manner as in Example 22(a). There was obtained a THF solution of cyclohexyl magnesium chloride.

The THF solution of cyclohexyl magnesium chloride so obtained was reacted with tetrachlorosilane and then with methanol in the same manner as in Example 23(a). The resulting reaction solution was post-treated in the same manner as in Example 23(a), to obtain the organic layer containing tri-cyclohexylmethoxysilane.

The resulting organic layer was treated with 35% hydrochloric acid in the same manner as in Example 15(d). The organic layer was separated from the aqueous layer and was concentrated under a reduced pressure. The resulting crystals was recrystallized from n-hexane to afford 34 g of tricyclohexylchlorosilane (yield; 55%).

EXAMPLE 28

The THF solution of isopropyl magnesium chloride as obtained in Example 17(a) was reacted with methanol in the same manner as in Example 22(b), thereby to obtain a solution of a mixture comprising methoxy magnesium chloride so produced and the unreacted isopropyl magnesium chloride. Instead of tetrachlorosilane used in Example 22(c), 29.9 g (0.2 moles) of methyltrichlorosilane was used, and this was added to said THF solution comprising methoxy magnesium chloride and the isopropyl magnesium chloride obtained as above. Then the reaction was conducted in the same manner as in Example 22(c). The resulting Grignard reaction solution was post-treated with the saturated aqueous ammonium chloride solution same as in Example 22(c), with using a reduced amount of 120 ml (not 160 ml) of the aqueous NH₄Cl solution, thus to obtain an organic layer containing diisopropylmethylmethoxysilane.

The resulting organic layer was treated with 35% hydrochloric acid in the same manner as in Example 15(d). The organic layer was separated from the aqueous layer and was subjected to a fractional distillation under a reduced pressure, to afford 27 g of diisopropylmethylchlorosilane as a fraction boiling at 57° C.-59° C./43 mm Hg (yield; 80%).

EXAMPLE 29

Instead of isopropyl chloride used in Example 17(a), 61.1 g (0.66 moles) of sec-butyl chloride was used. This was reacted with metallic magnesium in THF in the same manner as in Example 17(a). Thus, there was obtained a THF solution of sec-butyl magnesium chloride. The resulting THF solution of sec-butyl magnesium chloride so produced was reacted with methanol in the same manner as in Example 22(b). There was thus obtained a solution of a mixture comprising methoxy magnesium chloride so produced and the unreacted sec-butyl magnesium chloride.

To said solution comprising methoxy magnesium chloride and sec-butyl magnesium chloride which was obtained as above, was added 29.9 g (0.2 moles) of methyltrichlorosilane in place of tetrachlorosilane used in Example 22(c). Then, the reaction was conducted in the same manner as in Example 22(c) The resulting Grignard reaction solution was post-treated in the same manner as in Example 22(c) except that the amount of the saturated aqueous ammonium chloride solution was reduced to 120 ml from the 160 ml as used in Example 22(c). Thus, there was obtained an organic layer containing di-sec-butylmethylmethoxysilane.

The resulting organic layer containing di-sec-butyl methylmethoxysilane was treated with 35% hydrochloric acid in the same manner as in Example 15(d). The organic layer was separated from the aqueous layer and was subjected to a fractional distillation under a reduced pressure to afford 32 g of di-sec-butylmethylchlorosilane as a fraction boiling at 78° C.-81° C./16 mm Hg (yield; 81%).

EXAMPLE 30

(a) Synthesis of a Tri-Organo-Mono-Alkoxysilane from a Tri-Organo-Hydrosilane Compound A 300 ml-capacity, four-necked flask fitted with a stirrer, a thermometer and a Dimroth was charged with 200 g of a 28% methanolic solution of sodium methylate. The content of the flask was heated to have a temperature of 60° C., and into the flask was added dropwise 31.7 g (0.2 moles) of triisopropyl-hydrosilane through a dropping funnel under stirring over 30 minutes. The resulting mixture was stirred for 10 hours under refluxing condition. The resulting reaction solution was separated into the lower layer comprising mainly a methanolic solution of sodium methylate and into the upper organic layer containing mainly triisopropylmethoxysilane. The lower layer was separated and discured, affording the upper organic layer made of a reaction solution containing triisopropyl-methoxysilane.

(b) Synthesis of a Tri-Organo-Chlorosilane (by the Third Aspect Process of this Invention)

The triisopropylmethoxysilane present in the upper organic layer as obtained in (a) above was reacted with 35% hydrochloric acid in the same manner as in Example 15(d). The organic layer in the resulting reaction solution was then separated from the aqueous layer and was subjected to a fractional distillation under a reduced pressure, to afford 31 g of triisopropylchlorosilane as a fraction boiling at 78° C.-80° C./10 mm Hg (yield; 80%).

EXAMPLE 31

The procedure of Example 30(a) was repeated except that triisopropylhydrosilane used in Example 30(a) was replaced by 23.3 g (0.2 moles) of tert-butyldimethylhydrosilane, and the reaction with sodium mathylate was effected. Thus, there was obtained the reaction solution containing tert-butyldimethylmethoxysilane.

To the resulting reaction solution containing tert-butyldimethylmethoxysilane was added 300 g of a 35% hydrochloric acid, and the resultant mixture was stirred at 20° C. for 10 hours. There was produced and deposited tert-butyldimethylchlorosilane as crystals, which were then separated from the aqueous layer by filtration. The crystals as obtained were distilled at atmospheric pressure to afford 24 g of tert-butyldimethylchlorosilane as a fraction boiling at 124° C.-125° C. (yield; 78%).

Now, Procedure (A) for practicing the fourth aspect process of this invention is illustrated by reference to Examples 32-39 and Example 42, and Procedure (B) for practicing the same process is also illustrated with reference to Examples 40-41.

EXAMPLE 32

(a) Preparation of Grignard Reagent

A one liter-capacity, four-necked flask fitted with a stirrer, a thermometer and a Dimroth was charged with 21.4 g (0.88 moles) of metallic magnesium, 360 ml of tetrahydrofuran and a small amount of iodine. To the resulting mixture was added dropwise 69.1 g (0.88 moles) of isopropyl chloride under a nitrogen gas atmosphere at a temperature of the mixture of 40° C.-50° C. over 1 hour. The resulting reaction mixture was then heated at 50° C. under stirring for 1 hour, thus affording the reaction solution containing isopropyl magnesium chloride (Grignard reagent) so produced.

(b) Preparation of a Reaction Solution Containing Methoxy Magnesium Chloride

To the tetrahydrofuran solution of isopropyl magnesium chloride (that is, an isopropyl Grignard reagent) as obtained in (a) above, was added 6.4 g (0.2 moles) of methanol dropwise at 20-30° C. over 30 minutes, followed by effecting the reaction (by Procedure (A) for practicing the fourth aspect process of this invention). There was thus obtained a reaction solution containing both the remaining unreacted isopropyl Grignard reagent and the so produced methoxy magnesium chloride.

(c) Grignard Reaction

To the reaction solution in tetrahydrofuran containing the isopropyl Grignard reagent and methoxy magnesium chloride as obtained in (b) above, was added dropwise 34.0 g (0.2 moles) of silicon tetrachloride (that is, tetrachlorosilane) at 30° C.-40° C. over 1 hour. The resulting reaction mixture was then heated at a temperature of the mixture of 75° C. under stirring for 4 hours so as to progress the reactions between the reactive components. After the finish of the reactions, the resulting reaction solution was analyzed by a gas chromatography, thus confirming the formation of triisopropylmethoxysilane in a yield of 72%.

After the completion of the reactions, there was added dropwise 160 ml of a saturated aqueous ammonium chloride solution to the resulting reaction solution to dissolve the magnesium salt. Subsequently, the organic layer in the reaction solution was separated from the aqueous layer and was distilled to give a fraction boiling at 85° C.-86° C./20 mm Hg. Thus, there was afforded 23 g of triisopropylmethoxysilane as said fraction (yield; 60%).

EXAMPLE 33

Procedure of Example 32(b) was repeated except that there was used 14.8 g (0.2 moles) of n-butanol instead of methanol. The tetrahydrofuran solution of isopropyl magnesium chloride (the isopropyl Grignard reagent) was reacted with n-butanol in the same manner as in Example 32(b). So, there was given the reaction solution containing the remaining unreacted isopropyl magnesium chloride and the so produced n-butoxy magnesium chloride.

Then, Grignard reaction was progressed by adding $SiCl_4$ to the said reaction solution and further was effected in the same manner as in Example 32(c). After the finish of the reaction, the resulting reaction solution was post-treated in the same manner as in Example 32(c). The organic layer as separated was distilled to afford 28 g of triisopropyl-n-butoxysilane as a fraction boiling at 98° C.-102° C./12 mm Hg (yield; 59%).

EXAMPLE 34

Procedure of Example 32(b) was repeated except that there was used 8.8 g (0.2 moles) of ethylene oxide instead of methanol. Thus, the tetrahydrofuran solution of isopropyl magnesium chloride was reacted with ethylene oxide in the same manner as in Example 32(b). So there was given the reaction solution containing the remaining unreacted isopropyl magnesium chloride and the so produced 3-methylbutoxy magnesium chloride.

Then, Grignard reaction was progressed by adding silicon tetrachloride to said reaction solution and was further effected in the same manner as in Example 32(c). After the finish of the reaction, the resulting reaction solution was post-treated in the same manner as in Example 32(c). The organic layer as separated was distilled to afford 29 g of triisopropyl-3-methylbutoxysilane as a fraction boiling at 118° C.-120° C./5 mm Hg (yield; 590).

EXAMPLE 35

The procedure of Example 32(a) was repeated except that there was used 81.5 g (0.88 moles) of sec-butyl chloride in place of isopropyl chloride. Then, sec-butyl chloride was reacted with 21.4 g (0.88 moles) of metallic magnesium in tetrahydrofuran (THF) in the same manner as in Example 32(a). So, there was given a THF solution of sec-butyl magnesium chloride (Grignard reagent).

To the above THF solution of the Grignard reagent, methanol was added and then the reaction was effected in the same manner as in Example 32(b), giving a reaction solution containing the remaining unreacted sec-butyl magnesium chloride and the so produced methoxy magnesium chloride.

Then, Grignard reaction was progressed by adding silicon tetrachloride to said reaction solution and further was effected in the same manner as in Example 32(c). After the finish of the reaction, the resulting reaction solution was post-treated in the same manner as in Example 32(c). The organic layer as separated was distilled to afford 26 g of tri-sec-butylmethoxysilane as a fraction boiling at 89° C.-91° C./5 mm Hg (yield; 55%).

EXAMPLE 36

The procedure of Example 32(a) was repeated except that there was used 104.4 g (0.88 moles) of cyclohexyl chloride in place of isopropyl chloride. Then cyclohexyl chloride was reacted with 21.4 g (0.88 moles) of metallic magnesium in THF in the same manner as in Example 32(a). So, there was given a THF solution of cyclohexyl magnesium chloride (Grignard reagent).

To the above THF solution of the Grignard reagent, 14.8 g (0.2 moles) of n-butanol was added in place of methanol used in Example 32(b). The reaction was further effected in the same manner as in Example 32(b). Thus there was given a reaction solution containing the remaining unreacted cyclohexyl magnesium chloride and the so produced n-butoxy magnesium chloride.

Then, Grignard reaction was progressed by adding silicon tetrachloride to the resulting reaction solution and was further effected in the same manner as in Example 32(c). After the finish of the reaction, the resulting reaction solution was post-treated in the same manner as in Example 32(c). The organic layer as separated was concentrated to afford crude crystals of tricyclohexyl-n-butoxysilane. Recrystallization from hexane gave 40 g of tricyclohexyl-n-butoxysilane (yield; 55%).

EXAMPLE 37

The procedure of Example 32(a) was repeated except that the amount of metallic magnesium used was decreased from 21.4 g (0.88 moles) to 16.0 g (0.66 moles), the amount of THF was decreased from 360 ml to 270 ml and the amount of isopropyl chloride was decreased from 69.1 g (0.88 moles) to 51.8 g (0.66 moles). Then the metallic magnesium was reacted with isopropyl chloride in the same manner as in Example 32(a). There was thus obtained a THF solution of isopropyl magnesium chloride (Grignard reagent).

To the above THF solution of the Grignard reagent, methanol was then added and the reaction was effected in the same manner as in Example 32(b), giving a reaction solution containing the remaining unreacted isopropyl magnesium chloride and the so produced methoxy magnesium chloride.

Then, Grignard reaction was progressed further by adding to said reaction solution 29.9 g (0.2 moles) of methyltrichlorosilane, instead of the silicon tetrachloride as used in Example 32(c). After the finish of the reaction, the resulting reaction solution was post-treated in the same manner as in Example 32(c) except that the amount of the saturated aqueous ammonium chloride solution used was decreased from 160 ml to 120 ml. The organic layer as separated was distilled to afford 27 g of diisopropylmethylmethoxysilane as a fraction boiling at 55° C.-56° C./43 mm Hg (yield; 81%).

EXAMPLE 38

The procedure of Example 35 was repeated except that the amount of metallic magnesium used was decreased from 21.4 g (0.88 moles) to 16.0 g (0.66 moles), the amount of THF was decreased from 360 ml to 270 ml and the amount of sec-butyl chloride was decreased from 81.5 g (0.88 moles) to 61.1 g (0.66 moles). Then the metallic magnesium was reacted with sec-butyl chloride in the same manner as in Example 32(a). There was thus obtained a THF solution of sec-butyl magnesium chloride (Grignard reagent).

To the above THF solution of the Grignard reagent of sec-butyl magnesium chloride, methanol was then added, and the reaction was made in the same manner as in Example 32(b). There was thus obtained a reaction solution containing the remaining unreacted sec-butyl magnesium chloride and the so produced methoxy magnesium chloride.

Then, Grignard reaction was effected further by adding to said reaction solution 29.9 g (0.2 moles) of methyltrichlorosilane, instead of silicon tetrachloride as used in Example 32(c). After the finish of the reaction, the resulting reaction solution was post-treated in the same manner as in Example 32(c), except that the amount of the saturated aqueous ammonium chloride solution used was decreased from 160 ml to 120 ml. The organic layer as separated was distilled to afford 32 g of di-sec-butylmethylmethoxysilane as a fraction boiling at 76° C.-78° C./16 mm Hg (yield; 82%).

EXAMPLE 39

The procedure of Example 36 was repeated except that the amount of metallic magnesium used was decreased from 21.4 g (0.88 moles) to 16.0 g (0.66 moles), the amount of THF was decreased from 360 ml to 270 ml and the amount of cyclohexyl chloride was decreased from 104.4 g (0.88 moles) to 78.3 g (0.66 moles). The reaction was effected in the same manner as in Example 32(a). There was thus obtained a THF solution of cyclohexyl magnesium chloride (Grignard reagent).

To the above THF solution of the Grignard reagent, cyclohexyl magnesium chloride, methanol was then added. The reaction was then effected in the same manner as in Example 32(b), thus to give a reaction solution containing the remaining unreacted cyclohexyl magnesium chloride and the so produced methoxy magnesium chloride.

Then, Grignard reaction was effected further by adding to said reaction solution 29.9 g (0.2 moles) of methyltrichlorosilane, instead of the silicon tetrachloride as used in Example 32(c). After the finish of the reaction, the resulting reaction was post-treated in the same manner as in Example 32(c) except that the amount of the saturated aqueous ammonium chloride solution used was decreased from 160 ml to 120 ml. The organic layer as separated was distilled to afford 41 g of dicyclohexylmethylmethoxysilane as a fraction boiling at 128° C.-129° C./7 mm Hg (yield; 83%).

EXAMPLE 40

To the THF solution of isopropyl magnesium chloride (Grignard reagent) used in Example 32(a), was added dropwise 34.0 g (0.2 moles) of silicon tetrachloride at 30-40° C. over 1 hour, with effecting further reaction (by Procedure B of the fourth aspect process of this invention).

To the resulting reaction mixture was then added 6.4 g (0.2 moles) of methanol dropwise at 30-40° C. over 30 minutes, and thus the reaction as intended was effected. The reaction solution now obtained was heated at 75° C. under stirring for 4 hours so as to proceed further reaction. The resulting reaction solution was analyzed by a gas chromatography, thus confirming the formation of triisopropylmethoxysilane in a yield of 73%.

To the resulting reaction solution above was added dropwise 160 ml of a saturated aqueous ammonium chloride solution to dissolve the magnesium salt. Then the organic layer as separated was distilled to afford a fraction boiling at 85° C.-86° C./20 mm Hg. Thus there was obtained 23 g of triisopropylmethoxysilane (yield; 61%).

EXAMPLE 41

A one liter-capacity, four-necked flask fitted with a stirrer, a thermometer and a Dimroth was charged with 34.0 g (0.2 moles) of silicon tetrachloride and 200 ml of THF. To the flask was added dropwise the THF solution of isopropyl magnesium chloride (Grignard reagent) as used in Example 32(a), at 30-40° C. over 1 hour, with accompanying some reaction.

To the reaction mixture so obtained was then added 6.4 g (0.2 moles) of methanol dropwise at 30-40° C. over 30 minutes, and the reaction was effected (by Procedure B of the fourth aspect process of this invention). The reaction solution now obtained was heated at 75° C. under stirring for 4 hours to proceed further reaction.

To the resulting reaction solution was added dropwise 160 ml of a saturated aqueous ammonium chloride solution to dissolve the magnesium salt. Then the organic layer was separated and was distilled to afford a fraction boiling at 85° C.-86° C./20 mm Hg. Thus, there was obtained 29 g of triisopropylmethoxysilane (yield; 77%).

EXAMPLE 42

(a) Preparation of Grignard Reagent

A 500 ml-capacity, four-necked flask fitted with a stirrer, a thermometer and a Dimroth was charged with 11.7 g (0.48 moles) of metallic magnesium, 200 ml of tetrahydrofuran (THF) and a small amount of iodine. To the flask was then added dropwise 37.7 g (0.48 moles) of isopropyl chloride at 40-50° C. under a nitrogen gas atmosphere over 1 hour. Then, the reaction mixture so obtained was heated at 50° C. under stirring for 1 hour, thus to effect the reaction and obtain a THF solution of isopropyl magnesium chloride (Grignard reagent) as produced.

(b) Grignard Reaction

To the THF solution of isopropyl magnesium chloride (Grignard reagent) as obtained in (a) above, was added dropwise 34.0 g (0.2 moles) of tetrachlorosilane at 30-40° C. over 1 hour. Then the mixture so obtained was heated at 75° C. under stirring for 4 hours to conduct the Grignard reaction. After the finish of the reaction, the resulting reaction solution was analyzed by a gas chromatography, confirming the formation of dichlorodiisopropylsilane in a yield of 76%.

(c) Preparation of Grignard Reagent

A one liter-capacity, four-necked flask fitted with a stirrer, a thermometer and a Dimroth was charged with 4.9 g (0.20 moles) of metallic magnesium, 80 ml of tetrahydrofuran (THF) and a small amount of iodine. To the flask was then added dropwise 15.7 g (0.20 moles) of isopropyl chloride at 40-50° C. under a nitrogen gas atmosphere over 1 hour. Then, the reaction mixture so obtained was heated at 50° C. under stirring for 1 hour, thus to effect the reaction and obtain a THF solution of isopropyl magnesium chloride.

(d) Preparation of Methoxy Magnesium Chloride Solution

To the THF solution of isopropyl magnesium chloride (Grignard reagent) as obtained in (c) above, was added dropwise 6.4 g (0.2 moles) of methanol at 20-30° C. over 30 minutes. The reaction was effected to obtain a solution of methoxy magnesium chloride.

(e) Production of a Monoalkoxy-Dialkylmonochlorosilane

To the solution of methoxy magnesium chloride as obtained in (d) above, was added dropwise the solution containing dichlorodiisopropylsilane as obtained in (b) above, at 30-40° C. over 1 hour. Then, the reaction mixture so obtained was heated at 75° C. under stirring for 4 hours to conduct the reaction. The resulting reaction solution was analyzed by a gas chromatography, confirming the formation of chlorodiisopropylmethoxysilane in a yield of 74%.

(f) Preparation of Grignard Reagent

A 200 ml-capacity, four-necked flask fitted with a stirrer, a thermometer and a Dimroth was charged with 4.9 g (0.20 moles) of metallic magnesium, 80 ml of tetrahydrofuran (THF) and a small amount of iodine. To the flask was then added dropwise 15.7 g (0.20 moles) of isopropyl chloride at 40-50° C. under a nitrogen gas atmosphere over 1 hour. Then, the reaction mixture so obtained was heated at 50° C. under stirring for 1 hour, thus to effect the reaction and obtain a THF solution of isopropyl magnesium chloride (Grignard reagent) as produced.

(g) Grignard Reaction

To the solution containing chlorodiisopropylmethoxysilane as obtained in (e) above, was added dropwise the THF solution of isopropyl magnesium chloride (Grignard reagent) as obtained in (f) above, at 30-40° C. over 1 hour. Then the reaction mixture so obtained was heated at 75° C. under stirring for 4 hours to conduct the reaction. The resulting reaction solution was analyzed by a gas chromatography, confirming the formation of triisopropylmethoxysilane in a yield of 72%.

After the finish of the reaction, to the resulting reaction solution was added dropwise 160 ml of a saturated aqueous ammonium chloride solution to dissolve the magnesium salt. Then the organic layer was separated and was fractionally distilled under a reduced pressure to afford 23 g of triisopropylmethoxysilane as a fraction boiling at 85° C.-86° C./20 mm Hg (yield; 60%).

EXAMPLE 43

(a) Preparation of Grignard Reagent

A 200 ml-capacity, four-necked flask fitted with a stirrer, a thermometer and a Dimroth was charged with 9.7 g (0.40 moles) of metallic magnesium, 165 ml of tetrahydrofuran (THF) and a small amount of iodine. To the flask was then added dropwise 31.4 g (0.40 moles) of isopropyl chloride at 40-50° C. under a nitrogen gas atmosphere over 1 hour. Then, the reaction mixture so obtained was heated at 50° C. under stirring for 1 hour, thus to effect the reaction and obtain a THF solution of isopropyl magnesium chloride (Grignard reagent) as produced.

(b) Grignard Reaction

A one liter-capacity, four-necked flask fitted with a stirrer, a thermometer and a Dimroth was charged with 34.0 g (0.2 moles) of tetrachlorosilane. To the latter was then added dropwise the THF solution of isopropyl magnesium chloride (Grignard reagent) as prepared in (a) above, at 30-40° C. over 1 hour. To the mixture so obtained was added 150 ml of toluene. The resultant mixture was stirred at 90° C. for 4 hours to conduct the Grignard reaction as intended. Thus, there was obtained a solution containing dichlorodiisopropylsilane.

(c) Production of a Mono-Alkoxy-Dialkylmonochlorosilane

To the solution containing dichlorodiisopropylsilane as obtained in (b) above, was added dropwise 6.4 g (0.2 moles) of methanol at 10-25° C. over 1 hour. Then, the reaction mixture so obtained was heated at 50° C. under stirring for 1 hour, thus to effect the reaction and obtain a solution containing chlorodiisopropylmethoxysilane.

(d) Preparation of Grignard Reagent

A 200 ml-capacity, four-necked flask fitted with a stirrer, a thermometer and a Dimroth was charged with 6.3 g (0.26 moles) of metallic magnesium, 105 ml of tetrahydrofuran (THF) and a small amount of iodine. To the flask was then added dropwise 20.4 g (0.26 moles) of isopropyl chloride at 40-50° C. under a nitrogen gas atmosphere over 1 hour. Then, the reaction mixture was so obtained heated at 50° C. under stirring for 1 hour, thus to effect the reaction and obtain a THF solution of isopropyl magnesium chloride as produced.

(e) Grignard Reaction

To the THF solution containing chlorodiisopropylmethoxysilane as obtained in (c) above, was added dropwise the THF solution of isopropyl magnesium chloride (Grignard reagent) as obtained in (d) above, at 30-40° C. over 1 hour. Then, the reaction mixture so obtained was heated at 90° C. under stirring for 4 hours to conduct further the Grignard reaction.

To the resulting reaction solution was added dropwise 120 ml of a saturated aqueous ammonium chloride solution to dissolve the magnesium salt. After separating the organic layer, it was fractionally distilled under a reduced pressure to afford 27 g of triisopropylmethoxysilane as a fraction boiling at 85° C.-86° C./20 mm Hg (yield; 70%).

Industrial Applicability

As is explained hereinbefore, according to this invention, there are provided the novel processes for the production of tri-organo-monoalkoxysilanes which are useful in industries and also there is provided a novel process for the production of tri-organo-monochlorosilanes which are useful in industries. These novel processes provided by the first to fourth aspects of this invention are utilizable for industries.

What is claimed is:

1. A process for the production of a tri-organo-mono-(alkoxy, cycloalkyloxy or aralkyloxy)silane containing a bulky hydrocarbon group or groups R therein and having the formula (XXVa)

$$R_{3-(x+y)}(R^1)_x(R^2)_y Si(OR^7) \quad (XXVa)$$

wherein $R^1$ stands for a primary, secondary or tertiary alkyl group, a cycloalkyl group, an alkenyl group, an alkynyl group, an aryl group or an aralkyl group, $R^2$ stands for a secondary alkyl group, a tertiary alkyl group, a cycloalkyl group or an aryl group, and wherein R stands for a secondary alkyl group or a tertiary alkyl group or a cycloalkyl group, or R stands for an alkyl-substituted aromatic hydrocarbon group as defined below, and $R^7$ has the same meaning as $R^3$ defined below, or $R^7$ is a group of the formula —$CH_2$—$CH(R)$—$R^4$ where R and $R^4$ have the same meaning as defined below, and x stands for an integer of 0 or 1 and y stands for an integer of 0, 1 or 2, where the integers for x and y are to be within the range of $0 \leq (x+y) \leq 2$, characterized in that the process comprises reacting tetrachlorosilane or a di or mono-organo-di or trichlorosilane of the formula (XXI)

$$(R^1)_x(R^2)_y SiCl_{4-(x+y)} \quad (XXI)$$

wherein $R^1$ and $R^2$ have the same meanings as defined above and x and y each stand for an integer as defined above, with a Grignard reagent of the formula (XXII)

$$RMgX \quad (XXII)$$

wherein R stands for a secondary alkyl group or a tertiary alkyl group or a cycloalkyl group, or R stands for an alkyl-substituted aromatic hydrocarbon group of which the alkyl substituent is bonding to a carbon atom present in the aromatic hydrocarbon group, with said carbon atom being adjacent to the carbon atom of the aromatic hydrocarbon group that is bonding to the magnesium atom, and X stands for a chlorine, bromine or iodine atom, in a manner such that the reaction of tetrachlorosilane or the di or trichlorosilane of the formula (XXI) with the Grignard reagent of the formula (XXII) is effected with addition of and reaction with an alcohol of the formula (XXIII)

$$R^3OH \quad (XXIII)$$

wherein $R^3$ stands for a primary or secondary alkyl group, a cycloalkyl group or an aralkyl group, or an alkylene oxide or a glycidylether of the formula (XXIV)

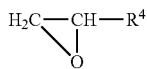 (XXIV)

wherein R⁴ stands for a hydrogen atom or an alkyl group of 1-8 carbon atoms, or R⁴ stands for an alkoxymethylene group, an alkenyloxymethylene group or an aryloxymethylene group of the formula —CH$_2$—O—R$^5$ where R$^5$ is a straight or branched chain alkyl group of 1-20 carbon atoms, an alkenyl group of 2-10 carbon atoms or an aryl group.

2. The process as claimed in claim 1, wherein the process comprises admixing and reacting at first the Grignard reagent of the formula (XXII) with the alcohol of the general formula (XXIII) or the alkylene oxide or glycidylether of the formula (XXIV), then adding to the so obtained reaction mixture containing therein the remaining Grignard reagent and the resulting reaction product of the reaction of the Grignard reagent with the alcohol or the alkylene oxide or glycidylether, an amount of tetrachlorosilane or a di or mono-organo-di or trichlorosilane of the formula (XXI), and effecting further reactions between the Grignard reagent, said reaction product and the added tetrachlorosilane or the added di or mono-organo-di or trichlorosilane present in the resultant mixture, to produce the tri-organo-mono-(alkoxy, cycloalkyloxy or aralkyloxy)silane of formula (XXVa).

3. The process as claimed in claim 1, wherein the process comprises admixing and reacting at first the Grignard reagent of the formula (XXII) with tetrachlorosilane or a di or mono-organo-di or trichlorosilane of the formula (XXI), then adding to the so obtained reaction mixture containing therein the Grignard reagent and the resulting reaction product of the reaction of the Grignard reagent with tetrachlorosilane or the di or mono-organo-di or trichlorosilane, an amount of the alcohol of the formula (XXIII) or the alkylene oxide or glycidylether of the formula (XXIV), and effecting further reactions between the Grignard reagent, said reaction product and the added alcohol or the added alkylene oxide or glycidylether present in the resultant mixture, to produce the tri-organo-mono-(alkoxy,cycloalkyloxy or aralkyloxy)silane of the formula (XXVa).

4. The process as claimed in claim 1, wherein the tri-organo-monoalkoxysilane of the formula (XXVa) produced finally is a triisopropylmonoalkoxysilane.

5. The process as claimed in claim 1, wherein the tri-organo-monoalkoxysilane of the formula (XXVa) produced finally is a tri-sec-butylmonoalkoxysilane.

6. The process as claimed in claim 1, wherein the tri-organo-monoalkoxysilane of the formula (XXVa) produced finally is a tricyclohexylmonoalkoxysilane.

* * * * *